United States Patent
Jia et al.

(10) Patent No.: US 11,603,363 B2
(45) Date of Patent: Mar. 14, 2023

(54) CRYSTALLINE FORM OF LNP023

(71) Applicant: Novartis AG, Basel (CH)

(72) Inventors: Zichen Jia, Basel (CH); Philipp Lustenberger, Allschwil (CH); Marie Meyer, Basel (CH); Massimo Moratto, Basel (CH)

(73) Assignee: Novartis AG, Basel (CH)

( * ) Notice: Subject to any disclaimer, the term of this patent is extended or adjusted under 35 U.S.C. 154(b) by 8 days.

(21) Appl. No.: 17/322,409

(22) Filed: May 17, 2021

(65) Prior Publication Data

US 2021/0371394 A1    Dec. 2, 2021

Related U.S. Application Data

(60) Provisional application No. 63/052,699, filed on Jul. 16, 2020, provisional application No. 63/026,637, filed on May 18, 2020.

(51) Int. Cl.
*C07D 401/06*    (2006.01)

(52) U.S. Cl.
CPC ........ *C07D 401/06* (2013.01); *C07B 2200/13* (2013.01)

(58) Field of Classification Search
CPC .......................... C07D 401/06; C07B 2200/13
See application file for complete search history.

(56) References Cited

FOREIGN PATENT DOCUMENTS

WO    2015/009616 A1    1/2015

OTHER PUBLICATIONS

Schubart, PNAS, Apr. 16, 2019, vol. 116(16), 7926-7931. (Year: 2019).*
Mainolfi, J Med Chem, 2020, vol. 63, 5697-5722. (Year: 2020).*
Mainolf et al., "Discovery of 4-((2 S,4 S)-4-Ethoxy-1-((5-methoxy-7-methyl-1 H-indol-4-yl)methyl)piperidin-2-yl)benzoic Acid (LNP023), a Factor B Inhibitor Specifically Designed To Be Applicable to Treating a Diverse Array of Complement Mediated Diseases," J Med Chem. 63(11):5697-5722 (2020).
Caira et al., "Crystalline Polymorphism of Organic Compounds," Topics in Current Chemistry, vol. 198. Springer Verlang: Berlin Heidelberg, pp. 163-208 (1998).
International Search Report for International Application No. PCT/IB2021/054225, dated Jul. 16, 2021 (15 pages).

* cited by examiner

*Primary Examiner* — D Margaret M Seaman
(74) *Attorney, Agent, or Firm* — Francine F. Li

(57) ABSTRACT

Described herein is a crystalline hydrate form of LNP023 hydrochloride and to a process for its preparation. Furthermore, described herein is a pharmaceutical composition comprising the crystalline hydrate form of LNP023 hydrochloride, and at least one pharmaceutically acceptable excipient. The pharmaceutical composition described herein can be used to treat a disease and disorder mediated by complement activation.

23 Claims, 7 Drawing Sheets

CRYSTALLINE FORM OF LNP023

CLAIM OF PRIORITY

This application claims priority from U.S. Provisional Application Ser. No. 63/026,637 filed May 18, 2020, and 63/052,699 filed Jul. 16, 2020, each of which is incorporated herein by reference in its entirety.

FIELD

Described herein is a crystalline form of LNP023 hydrochloride and to a process for its preparation. Also described herein is a pharmaceutical composition comprising a crystalline form of LNP023 hydrochloride, and at least one pharmaceutically acceptable excipient. The pharmaceutical composition described herein can be used for the treatment of a disease or disorder mediated by complement activation.

BACKGROUND

LNP023 belongs to the class of Factor B inhibitors of the complement pathway and acts by inhibiting or suppressing the amplification of the complement system caused by C3 activation irrespective of the initial mechanism of activation. It is currently under development for the treatment or prophylaxis of paroxysmal nocturnal hemoglobinuria (PNH), C3 glomerulopathy (C3G), immunoglobuline A nephropathy (IgAN), and membranous nephropathy (MN). LNP023 hydrochloride is chemically designated as 4-((2S,4S)-(4-ethoxy-1-((5-methoxy-7-methyl-1H-indol-4-yl)methyl)piperidin-2-yl))benzoic acid hydrochloride and can be represented by the following chemical structure according to Formula (A)

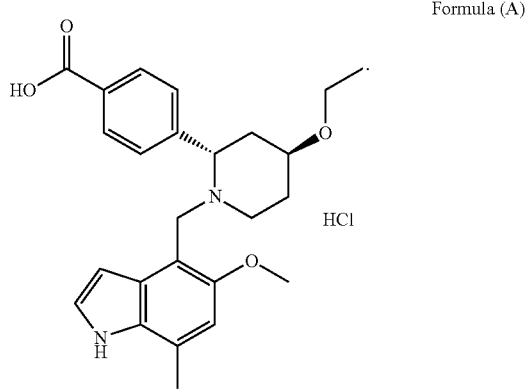 [SMILES: CCO[C@H]1CCN(Cc2c(OC)cc(C)c3[nH]ccc23)[C@H](c2ccc(C(=O)O)cc2)C1 ; Cl]

Formula (A)

LNP023 hydrochloride and methods for its preparation are disclosed in WO 2015/009616, which is incorporated herein by reference in its entirety. In Example 26d of WO 2015/009616, LNP023 hydrochloride is obtained as a crystalline solid by recrystallization of the amorphous material obtained and is characterized by X-ray powder diffraction. This crystalline form is referred to herein as Form A.

Different solid state forms of an active pharmaceutical ingredient often possess different properties. Differences in physicochemical properties of solid forms can play a crucial role for the improvement of pharmaceutical compositions, for example, pharmaceutical formulations with improved dissolution profile or with improved stability or shelf-life can become accessible due to an improved solid state form of an active pharmaceutical ingredient. Also, processing or handling of the active pharmaceutical ingredient during the formulation and manufacturing process may be improved. New solid state forms of an active pharmaceutical ingredient can thus have desirable processing properties. They can be easier to handle, are better suited for storage, or allow for better purification, compared to previously known solid forms.

Crystalline "Form A" of LNP023 HCl of WO 2015/009616 has certain properties which render it less suitable for large-scale manufacturing process. As such, a more stable form of LNP023 HCl is desired.

There is thus a need to provide a solid state form of LNP023 hydrochloride, which possess physicochemical properties allowing for the reliable production of a safe and efficacious drug product comprising LNP023 hydrochloride.

SUMMARY

The disclosure provides a crystalline hydrate form of LNP023 hydrochloride, which is hereinafter also referred to "Form HB". "Form HB" of LNP023 hydrochloride possesses favorable physicochemical properties for a drug substance intended for use in an oral solid dosage form.

The advantageous properties of Form HB of LNP023 include chemical stability, physical stability, hygroscopicity, solubility, dissolution, morphology, crystallinity, flowability, compactability and wettability. As a result, the properties make Form HB suitable for large-scale manufacturing processes.

In an embodiment, Form HB is a phase pure highly crystalline form of LNP023 hydrochloride physically and chemically stable during pharmaceutical processing and storage. Form HB is the thermodynamically more stable form and potential conversion into other forms can be minimized. Form A may under certain conditions convert to Form HB. The usage of the thermodynamically stable form of a compound is highly appreciated as conversions from, e.g., Form A to Form HB or polymorphic conversions, which may occur during manufacturing process and storage of a drug substance, can be excluded, when the most stable form is used. This ensures reliable bioavailability and therefore consistent efficacy of a drug product.

Abbreviations

PXRD powder X-ray diffraction
SXRD single crystal X-ray diffraction
FTIR Fourier transform infrared
ATR attenuated total reflection
DSC differential scanning calorimetry
DVS dynamic vapor sorption
TGA thermogravimetric analysis
MS mass spectrometry
NMR nuclear magnetic resonance
GC gas chromatography
KF Karl-Fischer
RH relative humidity
RT room temperature
w-% weight percent
vol-% volume percent

Definitions

In the context of the disclosure the following definitions have the indicated meaning, unless explicitly stated otherwise:

As used herein the term "room temperature" refers to a temperature in the range of from 20 to 30° C.

As used herein, the term "measured at a temperature in the range of from 20 to 30° C." refers to a measurement under standard conditions. Typically, standard conditions mean a temperature in the range of from 20 to 30° C., i.e. at room temperature. Standard conditions can mean a temperature of about 22° C.

The term "Form HB" as used herein, when describing a solid form of LNP023 hydrochloride, refers to a specific crystalline hydrate form of LNP023 hydrochloride, for example, the monohydrate form. This form is further defined herein and in the claims.

The term "Form A" as used herein, when describing a solid form of LNP023 hydrochloride, refers to a specific crystalline form of LNP023 hydrochloride as disclosed in WO 2015/009616. Form A of LNP023 hydrochloride can be characterized by having a powder X-ray diffractogram comprising peaks at 2-Theta angles of (11.6±0.1)°, (15.3±0.1)°, (16.5±0.1)°, (20.1±0.1)° and (23.3±0.1)°, when measured at a temperature in the range of from 20 to 30° C. with Cu-Kalpha$_{1,2}$ radiation having a wavelength of 0.15419 nm.

Form A is prepared according to WO 2015/009616 as follows (see example 26d):

To a solution of 4-((2S,4S)-(4-ethoxy-1-((5-methoxy-7-methyl-1H-indol-4-yl)methyl) piperidin-2-yl))benzoic acid (620 mg, 1.467 mmol) in H$_2$O/CH$_3$CN (10/3 mL) was added 5M aq. HCl (500 µL, 2.500 mmol). The reaction mixture was then lyophilized to provide an amorphous compound, which was then suspended in iPrOH (300 mL). The suspension was heated to 70° C. The suspension turned to a solution after 1.5 h. The solution was then cooled to room temperature with stirring for approx. 5 h to provide a solid. The resulting solid was collected by filtration and dried under high vacuum at 50° C. to afford the title compound as a crystalline solid. $^1$H NMR (HCl salt, 400 MHz, CD$_3$OD) δ 10.73 (br. s., 1H), 8.23 (d, J=8.44 Hz, 2H), 7.74 (d, J=8.44 Hz, 2H), 7.31-7.36 (m, 1H), 6.77 (s, 1H), 6.37 (dd, J=1.77, 3.12 Hz, 1H), 4.33 (d, J=12.72 Hz, 1H), 4.25 (d, J=12.72 Hz, 1H), 3.79-3.85 (m, 1H), 3.76 (s, 3H), 3.51-3.67 (m, 4H), 3.37-3.44 (m, 1H), 2.51 (s, 3H), 2.21-2.29 (m, 2H), 1.90-2.15 (m, 2H), 1.31 (t, J=6.97 Hz, 3H).

The X-ray powder diffraction pattern is described below in Table 1.

TABLE 1

| Angle 2-Theta ° | d value Angstrom | Intensity Count | Intensity % |
| --- | --- | --- | --- |
| 10.0 | 8.842 | 2532 | 41 |
| 11.6 | 7.631 | 4461 | 72 |
| 15.3 | 5.783 | 6231 | 100 |
| 16.5 | 5.360 | 4451 | 71 |
| 17.3 | 5.131 | 4119 | 66 |
| 20.1 | 4.418 | 4812 | 77 |
| 21.0 | 4.220 | 5911 | 95 |
| 22.8 | 3.900 | 3170 | 51 |
| 23.3 | 3.815 | 4537 | 73 |
| 25.3 | 3.520 | 3255 | 52 |
| 26.2 | 3.393 | 2968 | 48 |
| 31.0 | 2.887 | 1556 | 25 |

The term "reflection" with regard to powder X-ray diffraction as used herein, means peaks in an X-ray diffractogram, which are caused at certain diffraction angles (Bragg angles) by constructive interference from X-rays scattered by parallel planes of atoms in solid material, which are distributed in an ordered and repetitive pattern in a long-range positional order. Such a solid material is classified as crystalline material, whereas amorphous material is defined as solid material, which lacks long-range order and only displays short-range order, thus resulting in broad scattering. According to literature, long-range order e.g. extends over approximately 100 to 1000 atoms, whereas short-range order is over a few atoms only (see "*Fundamentals of Powder Diffraction and Structural Characterization of Materials*" by Vitalij K Pecharsky and Peter Y. Zavalij, Kluwer Academic Publishers, 2003, page 3).

The term "essentially the same" with reference to powder X-ray diffraction means that variabilities in peak positions and relative intensities of the peaks are to be taken into account. For example, a typical precision of the 2-Theta values is in the range of ±0.2° 2-Theta, e.g., in the range of ±0.1° 2-Theta. Thus, a peak that usually appears at 9.2° 2-Theta for example can appear between (9.2−0.2)° and (9.2+0.2)° 2-Theta, e.g., between (9.2−0.1)° and (9.2+0.1)° 2-Theta on most X-ray diffractometers under standard conditions. Furthermore, one skilled in the art will appreciate that relative peak intensities will show inter-apparatus variability as well as variability due to degree of crystallinity, preferred orientation, particle size, sample preparation and other factors known to those skilled in the art and should be taken as qualitative measure only.

The term "essentially the same" with reference to infrared spectrometry means that variabilities in peak positions and relative intensities of the peaks are to be taken into account. For example, a typical precision of the wavenumber values is in the range of ±4 cm$^{-1}$, e.g., in the range of ±2 cm$^{-1}$. Thus, a peak at 1692 cm$^{-1}$ for example can appear between (1692−4) and (1692+4) cm$^{-1}$, e.g., between (1692−2) and (1692+2) cm$^{-1}$ on most infrared spectrometers under standard conditions. Peak intensities can be derived from according figures, but one skilled in the art will appreciate that differences in peak intensities due to degree of crystallinity, sample preparation, measurement method and other factors can also occur in infrared spectroscopy. Peak intensities should therefore be taken as qualitative measure only.

Form HB of LNP023 hydrochloride described herein may be referred to herein as being characterized by graphical data "as shown in" a figure. Such data include, for example, powder X-ray diffraction and FTIR. The person skilled in the art understands that factors such as variations in instrument type, response and variations in sample directionality, sample concentration and sample purity may lead to small variations for such data when presented in graphical form, for example variations relating to the exact peak positions and intensities. However, a comparison of the graphical data in the figures herein with the graphical data generated for another or an unknown solid form and the confirmation that two sets of graphical data relate to the same crystal form is well within the knowledge of a person skilled in the art.

The terms "solid form" or "solid state form" as used herein interchangeably refer to any crystalline or amorphous phase of a compound.

As used herein, the term "amorphous" refers to a solid form of a compound that is not crystalline. An amorphous compound possesses no long-range order and does not display a definitive X-ray diffraction pattern with peaks.

As used herein the term "polymorph" refers to crystalline forms having the same chemical composition but different spatial arrangements of the molecules, atoms, or ions forming the crystal.

The term "co-crystal" as used herein refers to a crystalline material comprising two or more different molecular or ionic compounds in the same crystal lattice that are associated by nonionic and noncovalent bonds, wherein at least two of the individual molecular or ionic compounds are solids at room temperature.

The term "hydrate" as used herein, refers to a crystalline solid where either water is cooperated in or accommodated by the crystal structure e.g. is part of the crystal structure or entrapped into the crystal (water inclusions). Thereby, water can be present in a stoichiometric or non-stoichiometric amount. When water is present in stoichiometric amount, the hydrate may be referred to by adding Greek numeral prefixes. For example, a hydrate may be referred to as a hemihydrate or as a monohydrate depending on the water/compound stoichiometry. The water content can be measured, for example, by Karl-Fischer-Coulometry.

The terms "dehydrating" or "dehydration" as used herein, describe the at least partial removal of water from the crystal structure of the host molecule.

The term "solvate" as used herein, refers to a crystalline solid were either one or more organic solvent(s) is/are cooperated in or accommodated by the crystal structure e.g. is/are part of the crystal structure or entrapped into the crystal (solvent inclusions). Thereby, the one or more organic solvent(s) can be present in a stoichiometric or non-stoichiometric amount. When the one or more organic solvent(s) is/are present in stoichiometric amount(s), the solvate may be referred to by adding Greek numeral prefixes. For example, a solvate may be referred to as a hemisolvate or as a monosolvate depending on the solvent(s)/compound stoichiometry. The solvent content can be measured, for example, by GC, NMR, SXRD, or TGA/MS.

The term "isostructural solvate" as used herein, refers to solvates having the same space group with only small distortions of the unit cell dimensions and the same type of molecular network of the host molecule. Isostructural solvates as defined herein, differ in the type of organic solvent(s) present as guest molecule(s).

The terms "desolvating" or "desolvation" as used herein, describe the at least partial removal of organic solvent from the crystal structure of the host molecule.

The terms "anhydrous form" or "anhydrate" as used herein refer to a crystalline solid where no water is cooperated in or accommodated by the crystal structure. Anhydrous forms may still contain residual water, which is not part of the crystal structure but may be adsorbed on the surface or absorbed in disordered regions of the crystal. Typically, an anhydrous form does not contain more than 3.0 w-%, e.g., not more than 1.0 w-% of water, based on the weight of the crystalline form.

The term "non-solvated" as used herein, when talking about a crystalline solid indicates that no organic solvent is cooperated in or accommodated by the crystal structure. Non-solvated forms may still contain residual organic solvents, which are not part of the crystal structure but may be adsorbed on the surface or absorbed in disordered regions of the crystal. In an embodiment, a non-solvated form does not contain more than 3.0 w-%, e.g., not more than 1.0 w-%. In an embodiment, a non-solvated form does not contain more than 0.5 w-% of organic solvents, based on the weight of the crystalline form.

As used herein, the term "mother liquor" refers to the solution remaining after crystallization of a solid from said solution.

The term "antisolvent" as used herein refers to liquids which reduce the solubility of LNP023 hydrochloride in a solvent.

A "predetermined amount" as used herein with regard to LNP023 hydrochloride refers to the initial amount of LNP023 hydrochloride used for the preparation of a pharmaceutical composition having a desired dosage strength of LNP023 hydrochloride.

The term "therapeutically effective amount" as used herein with regard to LNP023 hydrochloride encompasses an amount of LNP023 hydrochloride, which causes the desired therapeutic, or prophylactic effect.

The term "non-hygroscopic" as used herein refers to an increase in mass (due to water uptake) of less than 0.2% at 80% RH at 25° C., based on the weight of the compound.

The term "equant" as used herein with regards to crystal shape refers to crystals which are equidimensional, such as cubes or spheres.

The terms "plate" or "plate-like" as used herein with regards to crystal shape refer to flat, tabular crystals having similar breadth and width, which are thicker than flakes.

The terms "flake" or "flake-like" as used herein with regards to crystal shape refer to thin, flat crystals that have similar breadth and width, which are thinner than plates.

The terms "needle" or "needle-like" as used herein with regards to crystal shape refer to acicular, thin and highly elongated crystals having similar width and breadth.

The term "columns" or "columnar" as used herein interchangeably with regards to crystal shape refers to elongated, prismatic crystals having greater width and thickness than needles.

Such crystal habit definitions are consistent with those usually used in the art, e.g. see "Polymorphism in the Pharmaceutical Industry" edited by Rolf Hilfiker (Wiley-VCH, 2006); Chapter 7, Light Microscopy (Gary Nichols).

As used herein, the term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "substantially free of any other solid form" with reference to a composition comprising a particular solid form of LNP023 hydrochloride means that the composition includes at most 20 w-% (weight percent), at most 15 w-%, at most 10 w-%, at most 9 w-%, at most 8 w-%, at most 7 w-%, at most 6 w-%, at most 5 w-%, at most 4 w-%, at most 3 w-%, at most 2 w-%, at most 1 w-%, at most 0.5 w-%, or at most 0.1 w-%, or any weight percentage between 80 and 100 w-% of any other solid form of LNP023 hydrochloride, based on the weight of the composition.

As used herein, "substantially pure," when used in reference to a form, means a compound having a purity greater than 90 w-%, including greater than 90, 91, 92, 93, 94, 95, 96, 97, 98, and 99 w-%, and also including equal to about 100 w-% of a particular solid form of LNP023 hydrochloride, based on the weight of the compound. The remaining material comprises other form(s) of the compound, or reaction impurities or processing impurities arising from its preparation. For example, a crystalline form of LNP023 hydrochloride may be deemed substantially pure in that it has a purity greater than 90 w-%, as measured by means that are at this time known and generally accepted in the art, where the remaining less than 10 w-% of material comprises other form(s) of LNP023 hydrochloride, reaction impurities, or processing impurities.

As used herein, the term "subject" is intended to mean human. Exemplary human subjects include a human patient (referred to as a patient) having a disorder, e.g., a disorder described herein or a normal subject.

The term "physically stable," as used herein, means that a particular free base or salt form does not change into one or more different physical forms (e.g., different solid forms as measured by XRPD, DSC, etc.) when subjected to specified conditions, e.g., room temperature ambient humidity or 40° C./75% relative humidity, for a specified period of time, e.g., 1 day, 2 days, 3 days, 1 week, 2 weeks, 1 month, 2 months, 3 months, 6 months, 12 months, 18 months, 24 months, or longer. In some embodiments, less than 25% of the form of a compound changes into one or more different physical forms when subjected to specified conditions. In some embodiments, less than about 20%, less than about 15%, less than about 10%, less than about 5%, less than about 3%, less than about 1%, less than about 0.5% of the form of a particular compound changes into one or more different physical forms of that particular compound when subjected to specified conditions. In some embodiments, no detectable amount of the particular form of a compound changes into one or more different physical forms of the compound.

The term "chemically stable," as used herein, means that the chemical structure of a particular compound, does not change into another compound (e.g., decompose) when subjected to specified conditions, e.g., room temperature ambient humidity or 40° C./75% relative humidity, for a specified period of time, e.g., 1 day, 2 days, 3 days, 1 week, 2 weeks, 1 month, 2 months, 3 months, 6 months, 12 months, 18 months, 24 months, or longer. In some embodiments, less than 25% of the form of a particular compound changes into one or more other compounds when subjected to specified conditions. In some embodiments, less than about 20%, less than about 15%, less than about 10%, less than about 5%, less than about 3%, less than about 1%, less than about 0.5% of the form of a particular compound changes into one or more other compounds when subjected to specified conditions. In some embodiments, no detectable amount of the form of a particular compound changes into one or more different physical forms of that particular compound.

The term "pharmaceutically acceptable excipient" as used herein refers to substances, which do not show a significant pharmacological activity at the given dose and that are added to a pharmaceutical composition in addition to the active pharmaceutical ingredient. Excipients may take the function of vehicle, diluent, release agent, disintegrating agent, dissolution modifying agent, absorption enhancer, stabilizer or a manufacturing aid among others. Excipients may include fillers (diluents), binders, disintegrants, lubricants and glidants.

The terms "filler" or "diluent" as used herein refer to substances that are used to dilute the active pharmaceutical ingredient prior to delivery. Diluents and fillers can also serve as stabilizers.

As used herein the term "binder" refers to substances which bind the active pharmaceutical ingredient and pharmaceutically acceptable excipient together to maintain cohesive and discrete portions.

The terms "disintegrant" or "disintegrating agent" as used herein refers to substances which, upon addition to a solid pharmaceutical composition, facilitate its break-up or disintegration after administration and permits the release of the active pharmaceutical ingredient as efficiently as possible to allow for its rapid dissolution.

The term "lubricant" as used herein refers to substances which are added to a powder blend to prevent the compacted powder mass from sticking to the equipment during tableting or encapsulation process. They aid the ejection of the tablet from the dies and can improve powder flow.

The term "glidant" as used herein refers to substances which are used for tablet and capsule formulations in order to improve flow properties during tablet compression and to produce an anti-caking effect.

DETAILED DESCRIPTION OF THE DISCLOSURE

Crystalline Form

Figure 1:
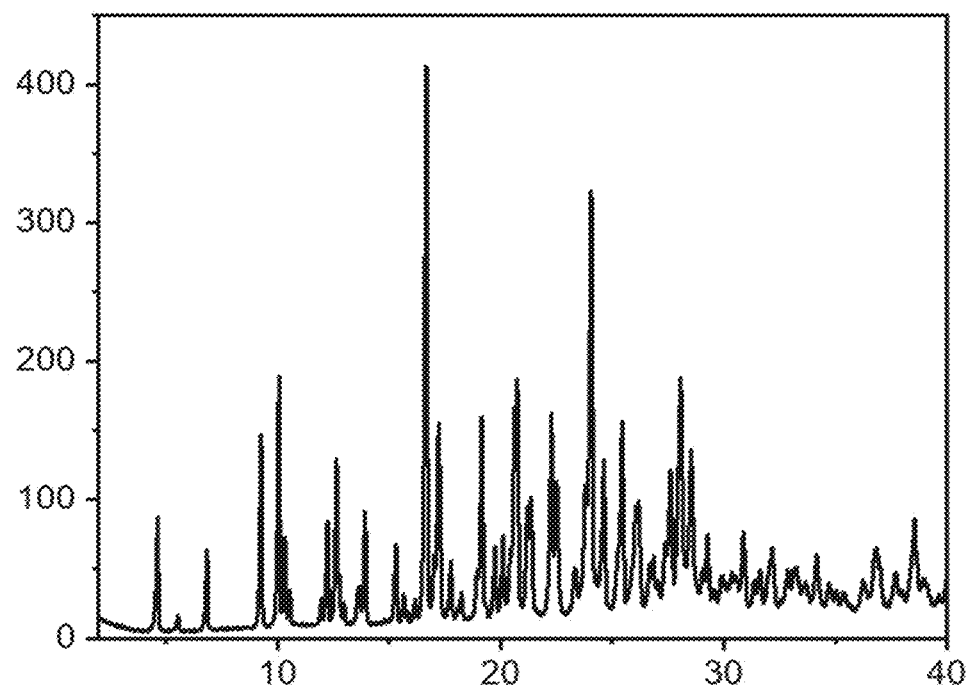
FIG. 1: illustrates a representative PXRD of Form HB of LNP023 hydrochloride described herein. The x-axis shows the scattering angle in ° 2-Theta, the y-axis shows the intensity of the scattered X-ray beam in counts of detected photons per second.

Exemplifications of Embodiments:

In an embodiment, the invention relates to a crystalline hydrate form of LNP023 hydrochloride, herein also referred to as "Form HB".

LNP023 hydrochloride can be represented by the following chemical structure according to Formula (A)

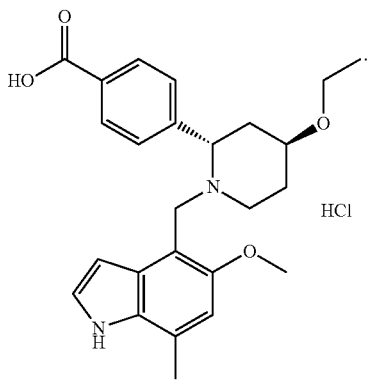

Formula (A)

Form HB of LNP023 hydrochloride described herein may be characterized by analytical methods well known in the field of the pharmaceutical industry for characterizing solids. Such methods comprise but are not limited to PXRD, SXRD, FTIR, DSC, DVS, TGA and SEM. It may be characterized by one of the aforementioned analytical methods or by combining two or more of them. In particular, Form HB of LNP023 hydrochloride described herein may be characterized by any one of the following embodiments or by combining two or more of the following embodiments.

Exemplification of PXRD Embodiments:

In an embodiment, the invention relates to a crystalline form of LNP023 hydrochloride (Form HB) characterized by the PXRD peaks identified at 2-Theta angles of (4.6±0.2)°, (9.2±0.2)°, and (19.1±0.2)°, when measured at a temperature in the range of from 20 to 30° C. with Cu-Kalpha$_{1,2}$ radiation having a wavelength of 0.15419 nm.

In an embodiment, the invention relates to a crystalline form of LNP023 hydrochloride (Form HB) characterized by the PXRD peaks identified at 2-Theta angles of (4.6±0.2)°, (6.8±0.2)°, (9.2±0.2)°, and (19.1±0.2)°, when measured at a temperature in the range of from 20 to 30° C. with Cu-Kalpha$_{1,2}$ radiation having a wavelength of 0.15419 nm.

In an embodiment, the invention relates to a crystalline form of LNP023 hydrochloride (Form HB) characterized by the PXRD peaks identified at 2-Theta angles of (4.6±0.2)°, (6.8±0.2)°, (9.2±0.2)°, (19.1±0.2)°, and (24.6±0.2)°, when measured at a temperature in the range of from 20 to 30° C. with Cu-Kalpha$_{1,2}$ radiation having a wavelength of 0.15419 nm. In an embodiment, the invention relates to a crystalline form of LNP023 hydrochloride (Form HB) characterized by the PXRD peaks identified at 2-Theta angles of (4.6±0.2)°, (6.8±0.2)°, (9.2±0.2)°, (12.2±0.2)°, (19.1±0.2)°, and (24.6±0.2)°, when measured at a temperature in the range of from 20 to 30° C. with Cu-Kalpha$_{1,2}$ radiation having a wavelength of 0.15419 nm.

In an embodiment, the invention relates to a crystalline form of LNP023 hydrochloride (Form HB) characterized by the PXRD peaks identified at 2-Theta angles of (4.6±0.2)°, (6.8±0.2)°, (9.2±0.2)°, (12.2±0.2)°, (19.1±0.2)°, (21.3±0.2)°, and (24.6±0.2)°, when measured at a temperature in the range of from 20 to 30° C. with Cu-Kalpha$_{L}$2 radiation having a wavelength of 0.15419 nm.

In an embodiment, the invention relates to a crystalline form of LNP023 hydrochloride (Form HB) characterized by the PXRD peaks identified at 2-Theta angles of (4.6±0.2)°, (6.8±0.2)°, (9.2±0.2)°, (12.2±0.2)°, (12.6±0.2)°, (16.6±0.2)°, (19.1±0.2)°, (21.3±0.2)°, and (24.6±0.2)°, when measured at a temperature in the range of from 20 to 30° C. with Cu-Kalpha$_{1,2}$ radiation having a wavelength of 0.15419 nm.

In an embodiment, the invention relates to a crystalline form of LNP023 hydrochloride (Form HB) characterized by the PXRD peaks identified at 2-Theta angles of (4.6±0.2)°, (6.8±0.2)°, (9.2±0.2)°, (10.0±0.2)°, (12.2±0.2)°, (12.6±0.2)°, (16.6±0.2)°, (19.1±0.2)°, (21.3±0.2)°, and (24.6±0.2)°, when measured at a temperature in the range of from 20 to 30° C. with Cu-Kalpha$_{1,2}$ radiation having a wavelength of 0.15419 nm.

In an embodiment, the invention relates to a crystalline form of LNP023 hydrochloride (Form HB) characterized by the PXRD peaks identified at 2-Theta angles of (4.6±0.2)°, (6.8±0.2)°, (9.2±0.2)°, (10.0±0.2)°, (12.2±0.2)°, (12.6±0.2)°, (16.6±0.2)°, (19.1±0.2)°, (21.3±0.2)°, and (24.6±0.2)°, when measured at a temperature in the range of from 20 to 30° C. with Cu-Kalpha$_{1,2}$ radiation having a wavelength of 0.15419 nm.

In an embodiment, the invention relates to a crystalline form of LNP023 hydrochloride (Form HB) characterized by the crystalline form of LNP023 hydrochloride (Form HB) can be characterized by the PXRD peaks identified at 2-Theta angles of (4.6±0.2)°, (6.8±0.2)°, (9.2±0.2)°, (10.0±0.2)°, (12.2±0.2)°, (12.6±0.2)°, (15.3±0.2)°, (16.6±0.2)°, (19.1±0.2)°, (21.3±0.2)°, and (24.6±0.2)°, when measured at a temperature in the range of from 20 to 30° C. with Cu-Kalpha$_{1,2}$ radiation having a wavelength of 0.15419 nm.

In an embodiment, the invention relates to a crystalline form of LNP023 hydrochloride (Form HB) characterized by the PXRD peaks identified at 2-Theta angles of (4.6±0.2)°, (6.8±0.2)°, (9.2±0.2)°, (10.0±0.2)°, (12.2±0.2)°, (12.6±0.2)°, (15.3±0.2)°, (16.6±0.2)°, (17.2±0.2)°, (19.1±0.2)°, (21.3±0.2)°, and (24.6±0.2)°, when measured at a temperature in the range of from 20 to 30° C. with Cu-Kalpha$_{1,2}$ radiation having a wavelength of 0.15419 nm.

In an embodiment, the invention relates to a crystalline form of LNP023 hydrochloride (Form HB) characterized by the PXRD peaks identified at 2-Theta angles of (4.6±0.2)°, (6.8±0.2)°, (9.2±0.2)°, (10.0±0.2)°, (12.2±0.2)°, (12.6±0.2)°, (15.3±0.2)°, (16.6±0.2)°, (17.2±0.2)°, (19.1±0.2)°, (20.7±0.2)°, (21.3±0.2)°, and (24.6±0.2)°, when measured at a temperature in the range of from 20 to 30° C. with Cu-Kalpha$_{1,2}$ radiation having a wavelength of 0.15419 nm.

In an embodiment, the invention relates to a crystalline form of LNP023 hydrochloride (Form HB) characterized by the PXRD peaks identified at 2-Theta angles of (4.6±0.2)°, (6.8±0.2)°, (9.2±0.2)°, (10.0±0.2)°, (12.2±0.2)°, (12.6±0.2)°, (15.3±0.2)°, (16.6±0.2)°, (17.2±0.2)°, (19.1±0.2)°, (20.7±0.2)°, (21.3±0.2)°, (24.0±0.2)°, and (24.6±0.2)°, when measured at a temperature in the range of from 20 to 30° C. with Cu-Kalpha$_{1,2}$ radiation having a wavelength of 0.15419 nm.

In an embodiment, the invention relates to a crystalline form of LNP023 hydrochloride (Form HB) characterized by the PXRD peaks identified at 2-Theta angles of (4.6±0.2)°, (6.8±0.2)°, (9.2±0.2)°, (10.0±0.2)°, (12.2±0.2)°, (12.6±0.2)°, (15.3±0.2)°, (16.6±0.2)°, (17.2±0.2)°, (19.1±0.2)°, (20.7±0.2)°, (21.3±0.2)°, (22.2±0.2)°, (24.0±0.2)°, and (24.6±0.2)°, when measured at a temperature in the range of from 20 to 30° C. with Cu-Kalpha$_{1,2}$ radiation having a wavelength of 0.15419 nm.

In an embodiment, the invention relates to a crystalline form of LNP023 hydrochloride (Form HB) characterized by the PXRD peaks identified at 2-Theta angles of (4.6±0.2)°, (6.8±0.2)°, (9.2±0.2)°, (10.0±0.2)°, (12.2±0.2)°, (12.6±0.2)°, (15.3±0.2)°, (16.6±0.2)°, (17.2±0.2)°, (19.1±0.2)°, (20.7±0.2)°, (21.3±0.2)°, (22.2±0.2)°, (24.0±0.2)°, (24.6±0.2)° and (28.0±0.2)°, when measured at a temperature in the range of from 20 to 30° C. with Cu-Kalpha$_{1,2}$ radiation having a wavelength of 0.15419 nm.

In an embodiment, the invention relates to a crystalline form of LNP023 hydrochloride (Form HB) characterized by the PXRD peaks identified at 2-Theta angles of (4.6±0.2)°, (6.8±0.2)°, (9.2±0.2)°, (12.2±0.2)°, (19.1±0.2)°, and (24.6±0.2)°, and at least one more peak selected from the group consisting of (10.0±0.2)°, (12.6±0.2)°, (15.3±0.2)°, (16.6±0.2)°, (17.2±0.2)°, (20.7±0.2)°, (21.3±0.2)°, (22.2±0.2)°, (24.0±0.2)°, and (28.0±0.2)°, when measured at a temperature in the range of from 20 to 30° C. with Cu-Kalpha$_{1,2}$ radiation having a wavelength of 0.15419 nm.

In another embodiment, the invention relates to a crystalline form of LNP023 hydrochloride (Form HB) characterized by the PXRD peaks identified at 2-Theta angles of:
(4.6±0.1)°, (9.2±0.1)°, and (19.1±0.1)°; or
(4.6±0.1)°, (6.8±0.1)°, (9.2±0.1)°, and (19.1±0.1)°; or
(4.6±0.1)°, (6.8±0.1)°, (9.2±0.1)°, (19.1±0.1)°, and (24.6±0.1)°; or
(4.6±0.1)°, (6.8±0.1)°, (9.2±0.1)°, (12.2±0.1)°, (19.1±0.1)° and (24.6±0.1)°; or
(4.6±0.1)°, (6.8±0.1)°, (9.2±0.1)°, (12.2±0.1)°, (19.1±0.1)°, (21.3±0.1)°, and (24.6±0.1)°; or
(4.6±0.1)°, (6.8±0.1)°, (9.2±0.1)°, (12.2±0.1)°, (12.6±0.1)°, (16.6±0.1)°, (19.1±0.1)°, (21.3±0.1)°, and (24.6±0.1)°; or
(4.6±0.1)°, (6.8±0.1)°, (9.2±0.1)°, (10.0±0.1)°, (12.2±0.1)°, (12.6±0.1)°, (16.6±0.1)°, (19.1±0.1)°, (21.3±0.1)°, and (24.6±0.1)°; or
(4.6±0.1)°, (6.8±0.1)°, (9.2±0.1)°, (10.0±0.1)°, (12.2±0.1)°, (12.6±0.1)°, (16.6±0.1)°, (19.1±0.1)°, (21.3±0.1)°, and (24.6±0.1)°; or
(4.6±0.1)°, (6.8±0.1)°, (9.2±0.1)°, (10.0±0.1)°, (12.2±0.1)°, (12.6±0.1)°, (15.3±0.1)°, (16.6±0.1)°, (19.1±0.1)°, (21.3±0.1)°, and (24.6±0.1)°; or
(4.6±0.1)°, (6.8±0.1)°, (9.2±0.1)°, (10.0±0.1)°, (12.2±0.2)°, (12.6±0.2)°, (15.3±0.2)°, (16.6±0.2)°, (17.2±0.2)°, (19.1±0.2)°, (21.3±0.2)°, and (24.6±0.2)°; or
(4.6±0.2)°, (6.8±0.2)°, (9.2±0.2)°, (10.0±0.2)°, (12.2±0.2)°, (12.6±0.2)°, (15.3±0.2)°, (16.6±0.2)°, (17.2±0.2)°, (19.1±0.2)°, (20.7±0.2)°, (21.3±0.2)°, and (24.6±0.2)°; or
(4.6±0.2)°, (6.8±0.2)°, (9.2±0.2)°, (10.0±0.2)°, (12.2±0.2)°, (12.6±0.2)°, (15.3±0.2)°, (16.6±0.2)°, (17.2±0.2)°, (19.1±0.2)°, (20.7±0.2)°, (21.3±0.2)°, (24.0±0.2)°, and (24.6±0.1)°; or
(4.6±0.1)°, (6.8±0.1)°, (9.2±0.1)°, (10.0±0.1)°, (12.2±0.1)°, (12.6±0.1)°, (15.3±0.1)°, (16.6±0.1)°, (17.2±0.1)°, (19.1±0.1)°, (20.7±0.1)°, (21.3±0.1)°, (22.2±0.1)°, (24.0±0.1)°, and (24.6±0.1)°; or
(4.6±0.1)°, (6.8±0.1)°, (9.2±0.1)°, (10.0±0.1)°, (12.2±0.2)°, (12.6±0.2)°, (15.3±0.1)°, (16.6±0.1)°, (17.2±0.1)°, (19.1±0.1)°, (20.7±0.1)°, (21.3±0.1)°, (22.2±0.1)°, (24.0±0.1)°, (24.6±0.1)° and (28.0±0.1)°, when measured at a temperature in the range of from 20 to 30° C. with Cu-Kalpha$_{1,2}$ radiation having a wavelength of 0.15419 nm.

In an embodiment, the invention relates to a crystalline form of LNP023 hydrochloride (Form HB) characterized by the PXRD peaks identified at 2-Theta angles of (4(4.6±0.1)°, (6.8±0.1)°, (9.2±0.1)°, (12.2±0.1)°, (19.1±0.1)°, and (24.6±0.1)°, and at least one more peak selected from the group consisting of (10.0±0.1)°, (12.6±0.1)°, (15.3±0.1)°, (16.6±0.1)°, (17.2±0.1)°, (20.7±0.1)°, (21.3±0.1)°, (22.2±0.1)°, (24.0±0.1)°, and (28.0±0.1)°, when measured at a temperature in the range of from 20 to 30° C. with Cu-Kalpha$_{1,2}$ radiation having a wavelength of 0.15419 nm.

Figure 2:
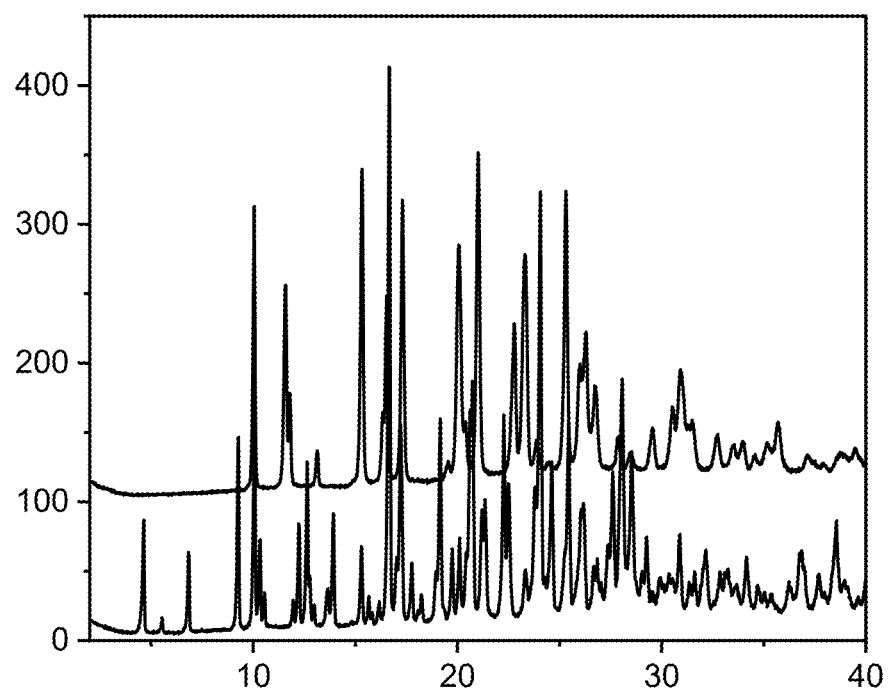
FIG. 2: illustrates a comparison of a representative PXRD of Form HB of LNP023 hydrochloride described herein (bottom) and a representative PXRD of Form A of LNP023 hydrochloride of WO 2015/009616 (top). The x-axis shows the scattering angle in ° 2-Theta. The powder X-ray diffractogram of Form A was shifted along the y-axis to separate the diffractograms for clarity. The y-axis is therefore arbitrary and was not labeled.

The PXRD of Form HB described herein can be clearly distinguished from the PXRD of Form A of WO 2015/009616 (see also the PXRD overlay displayed in FIG. 2 described herein). Form HB for example shows characteristic peaks at (4.6±0.1) and (9.2±0.1)° 2-Theta, whereas Form A shows no peak in the same ranges. According to page 176 of WO 2015/009616 among the four most characteristic peaks of Form A, one is the peak at 11.6° 2-Theta. In contrast, Form HB described herein shows no peak in the same range.

In another embodiment, the invention relates to a crystalline form of LNP023 hydrochloride (Form HB) which can be characterized by having a PXRD as described in one of the embodiments above, but not comprising a peak at a 2-Theta angle of (11.6±0.2)°, when measured at a temperature in the range of from 20 to 30° C. with Cu-Kalpha$_{1,2}$ radiation having a wavelength of 0.15419 nm.

In an embodiment, the invention relates to a crystalline form of LNP023 hydrochloride (Form HB) which can be characterized by having a PXRD as described above, but comprising no peaks at 2-Theta angles of (11.6±0.1)° 2-Theta, when measured at a temperature in the range of from 20 to 30° C. with Cu-Kalpha$_{1,2}$ radiation having a wavelength of 0.15419 nm.

In another embodiment, the invention relates to a crystalline form of LNP023 hydrochloride (Form HB) characterized by having a PXRD essentially the same as shown in FIG. 1 described herein, when measured at a temperature in the range of from 20 to 30° C. with Cu-Kalpha$_{1,2}$ radiation having a wavelength of 0.15419 nm.

The relative intensities of the peaks, e.g. as shown in FIG. 1 and as listed in Table 2, can be subject to a certain degree of variation due to the particle morphology of Form HB. In general, the morphology of many crystalline particles tends to give a specimen that exhibits some degree of preferred orientation in the specimen holder. This is particularly evident for needle-like or plate-like crystals when size reduction yields finer needles or platelets. Preferred orientation in the specimen influences the intensities of various peaks, so that some are more intense and others are less intense, compared to what would be expected from a completely random specimen.

Exemplification of FTIR Embodiments:

In an embodiment, the invention relates to a crystalline form of LNP023 hydrochloride (Form HB) characterized by having an FTIR spectrum comprising peaks at wavenumbers of (3452±4) cm$^{-1}$, (2875±4) cm$^{-1}$, and (1692±4) cm$^{-1}$.

In an embodiment, the invention relates to a crystalline form of LNP023 hydrochloride (Form HB) characterized by having an FTIR spectrum comprising peaks at wavenumbers of (3452±4) cm$^{-1}$, (2875±4) cm$^{-1}$, (1692±4) cm$^{-1}$, and (1439±4) cm$^{-1}$, when measured at a temperature in the range of from 20 to 30° C. with a diamond ATR cell.

In an embodiment, the invention relates to a crystalline form of LNP023 hydrochloride (Form HB) characterized by having an FTIR spectrum comprising peaks at wavenumbers of (3452±4) cm$^{-1}$, (2875±4) cm$^{-1}$, (1692±4) cm$^{-1}$, (1439±4) cm$^{-1}$, and (1243±4) cm$^{-1}$, when measured at a temperature in the range of from 20 to 30° C. with a diamond ATR cell.

In an embodiment, the invention relates to a crystalline form of LNP023 hydrochloride (Form HB) characterized by having an FTIR spectrum comprising peaks at wavenumbers of (3452±4) cm$^{-1}$, (2875±4) cm$^{-1}$, (1692±4) cm$^{-1}$, (1439±4)

cm$^{-1}$, (1243±4) cm$^{-1}$ and (767±4) cm$^{-1}$, when measured at a temperature in the range of from 20 to 30° C. with a diamond ATR cell.

In an embodiment, the invention relates to a crystalline form of LNP023 hydrochloride (Form HB) characterized by having an FTIR spectrum comprising peaks at wavenumbers of (3452±4) cm$^{-1}$, (2875±4) cm$^{-1}$, (2732±4) cm$^{-1}$, (1692±4) cm$^{-1}$, (1439±4) cm$^{-1}$, (1243±4) cm$^{-1}$, and (767±4) cm$^{-1}$, when measured at a temperature in the range of from 20 to 30° C. with a diamond ATR cell.

In an embodiment, the invention relates to a crystalline form of LNP023 hydrochloride (Form HB) characterized by having an FTIR spectrum comprising peaks at wavenumbers of (3452±4) cm$^{-1}$, (2875±4) cm$^{-1}$, (2732±4) cm$^{-1}$, (1709±4) cm$^{-1}$, (1692±4) cm$^{-1}$, (1658±4) cm$^{-1}$, (1439±4) cm$^{-1}$, (1243±4) cm$^{-1}$, and (767±4) cm$^{-1}$, when measured at a temperature in the range of from 20 to 30° C. with a diamond ATR cell.

In an embodiment, the invention relates to a crystalline form of LNP023 hydrochloride (Form HB) characterized by having an FTIR spectrum comprising peaks at wavenumbers of (3452±4) cm$^{-1}$, (2875±4) cm$^{-1}$, (2732±4) cm$^{-1}$, (1709±4) cm$^{-1}$, (1692±4) cm$^{-1}$, (1658±4) cm$^{-1}$, (1615±4) cm$^{-1}$, (1439±4) cm$^{-1}$, (1243±4) cm$^{-1}$ and (767±4) cm$^{-1}$, when measured at a temperature in the range of from 20 to 30° C. with a diamond ATR cell.

In an embodiment, the invention relates to a crystalline form of LNP023 hydrochloride (Form HB) characterized by having an FTIR spectrum comprising peaks at wavenumbers of (3452±4) cm$^{-1}$, (2875±4) cm$^{-1}$, (2732±4) cm$^{-1}$, (1709±4) cm$^{-1}$, (1692±4) cm$^{-1}$, (1658±4) cm$^{-1}$, (1615±4) cm$^{-1}$, (1601±4) cm$^{-1}$, (1439±4) cm$^{-1}$, (1243±4) cm$^{-1}$ and (767±4) cm$^{-1}$.

In an embodiment, the invention relates to a crystalline form of LNP023 hydrochloride (Form HB) characterized by having an FTIR spectrum comprising peaks at wavenumbers of (3452±4) cm$^{-1}$, (2875±4) cm$^{-1}$, (2732±4) cm$^{-1}$, (1709±4) cm$^{-1}$, (1692±4) cm$^{-1}$, (1658±4) cm$^{-1}$, (1615±4) cm$^{-1}$, (1601±4) cm$^{-1}$, (1515±4) cm$^{-1}$, (1439±4) cm$^{-1}$, (1243±4) cm$^{-1}$ and (767±4) cm$^{-1}$, when measured at a temperature in the range of from 20 to 30° C. with a diamond ATR cell.

In an embodiment, the invention relates to a crystalline form of LNP023 hydrochloride (Form HB) characterized by having an FTIR spectrum comprising peaks at wavenumbers of (3452±4) cm$^{-1}$, (2875±4) cm$^{-1}$, (2732±4) cm$^{-1}$, (1709±4) cm$^{-1}$, (1692±4) cm$^{-1}$, (1658±4) cm$^{-1}$, (1615±4) cm$^{-1}$, (1601±4) cm$^{-1}$, (1515±4) cm$^{-1}$, (1497±4) cm$^{-1}$, (1439±4) cm$^{-1}$, (1243±4) cm$^{-1}$ and (767±4) cm$^{-1}$, when measured at a temperature in the range of from 20 to 30° C. with a diamond ATR cell.

In an embodiment, the invention relates to a crystalline form of LNP023 hydrochloride (Form HB) characterized by having an FTIR spectrum comprising peaks at wavenumbers of (3452±4) cm$^{-1}$, (2875±4) cm$^{-1}$, (2732±4) cm$^{-1}$, (1709±4) cm$^{-1}$, (1692±4) cm$^{-1}$, (1658±4) cm$^{-1}$, (1615±4) cm$^{-1}$, (1601±4) cm$^{-1}$, (1515±4) cm$^{-1}$, (1497±4) cm$^{-1}$, (1461±4) cm$^{-1}$, (1439±4) cm$^{-1}$, (1243±4) cm$^{-1}$ and (767±4) cm$^{-1}$, when measured at a temperature in the range of from 20 to 30° C. with a diamond ATR cell.

In an embodiment, the invention relates to a crystalline form of LNP023 hydrochloride (Form HB) characterized by having an FTIR spectrum comprising peaks at wavenumbers of (3452±4) cm$^{-1}$, (2875±4) cm$^{-1}$, (2732±4) cm$^{-1}$, (1709±4) cm$^{-1}$, (1692±4) cm$^{-1}$, (1658±4) cm$^{-1}$, (1615±4) cm$^{-1}$, (1601±4) cm$^{-1}$, (1515±4) cm$^{-1}$, (1497±4) cm$^{-1}$, (1461±4) cm$^{-1}$, (1439±4) cm$^{-1}$, (1425±4) cm$^{-1}$, (1243±4) cm$^{-1}$ and (767±4) cm$^{-1}$, when measured at a temperature in the range of from 20 to 30° C. with a diamond ATR cell.

In an embodiment, the invention relates to a crystalline form of LNP023 hydrochloride (Form HB) characterized by having an FTIR spectrum comprising peaks at wavenumbers of (3452±4) cm$^{-1}$, (2875±4) cm$^{-1}$, (2732±4) cm$^{-1}$, (1709±4) cm$^{-1}$, (1692±4) cm$^{-1}$, (1658±4) cm$^{-1}$, (1615±4) cm$^{-1}$, (1601±4) cm$^{-1}$, (1515±4) cm$^{-1}$, (1497±4) cm$^{-1}$, (1461±4) cm$^{-1}$, (1439±4) cm$^{-1}$, (1425±4) cm$^{-1}$, (1384±4) cm$^{-1}$, (1243±4) cm$^{-1}$ and (767±4) cm$^{-1}$, when measured at a temperature in the range of from 20 to 30° C. with a diamond ATR cell.

In an embodiment, the invention relates to a crystalline form of LNP023 hydrochloride (Form HB) characterized by having an FTIR spectrum comprising peaks at wavenumbers of (3452±4) cm$^{-1}$, (2875±4) cm$^{-1}$, (2732±4) cm$^{-1}$, (1709±4) cm$^{-1}$, (1692±4) cm$^{-1}$, (1658±4) cm$^{-1}$, (1615±4) cm$^{-1}$, (1601±4) cm$^{-1}$, (1515±4) cm$^{-1}$, (1497±4) cm$^{-1}$, (1461±4) cm$^{-1}$, (1439±4) cm$^{-1}$, (1425±4) cm$^{-1}$, (1384±4) cm$^{-1}$, (1243±4) cm$^{-1}$, (1184±4) cm$^{-1}$ and (767±4) cm$^{-1}$, when measured at a temperature in the range of from 20 to 30° C. with a diamond ATR cell.

In an embodiment, the invention relates to a crystalline form of LNP023 hydrochloride (Form HB) characterized by having an FTIR spectrum comprising peaks at wavenumbers of (3452±4) cm$^{-1}$, (2875±4) cm$^{-1}$, (2732±4) cm$^{-1}$, (1709±4) cm$^{-1}$, (1692±4) cm$^{-1}$, (1658±4) cm$^{-1}$, (1615±4) cm$^{-1}$, (1601±4) cm$^{-1}$, (1515±4) cm$^{-1}$, (1497±4) cm$^{-1}$, (1461±4) cm$^{-1}$, (1439±4) cm$^{-1}$, (1425±4) cm$^{-1}$, (1384±4) cm$^{-1}$, (1243±4) cm$^{-1}$, (1184±4) cm$^{-1}$, (1069±4) cm$^{-1}$ and (767±4) cm$^{-1}$, when measured at a temperature in the range of from 20 to 30° C. with a diamond ATR cell.

In an embodiment, the invention relates to a crystalline form of LNP023 hydrochloride (Form HB) characterized by having an FTIR spectrum comprising peaks at wavenumbers of (3452±4) cm$^{-1}$, (2875±4) cm$^{-1}$, (2732±4) cm$^{-1}$, (1709±4) cm$^{-1}$, (1692±4) cm$^{-1}$, (1658±4) cm$^{-1}$, (1615±4) cm$^{-1}$, (1601±4) cm$^{-1}$, (1515±4) cm$^{-1}$, (1497±4) cm$^{-1}$, (1461±4) cm$^{-1}$, (1439±4) cm$^{-1}$, (1425±4) cm$^{-1}$, (1384±4) cm$^{-1}$, (1243±4) cm$^{-1}$, (1184±4) cm$^{-1}$, (1069±4) cm$^{-1}$, (767±4) cm$^{-1}$ and (739±4) cm$^{-1}$, when measured at a temperature in the range of from 20 to 30° C. with a diamond ATR cell.

In an embodiment, the invention relates to a crystalline form of LNP023 hydrochloride (Form HB) characterized by having an FTIR spectrum comprising peaks at wavenumbers of (3452±4) cm$^{-1}$, (3274±4) cm$^{-1}$, (2875±4) cm$^{-1}$, (2732±4) cm$^{-1}$, (1709±4) cm$^{-1}$, (1692±4) cm$^{-1}$, (1658±4) cm$^{-1}$, (1615±4) cm$^{-1}$, (1601±4) cm$^{-1}$, (1515±4) cm$^{-1}$, (1497±4) cm$^{-1}$, (1461±4) cm$^{-1}$, (1439±4) cm$^{-1}$, (1425±4) cm$^{-1}$, (1384±4) cm$^{-1}$, (1243±4) cm$^{-1}$, (1184±4) cm$^{-1}$, (1069±4) cm$^{-1}$, (767±4) cm$^{-1}$ and (739±4) cm$^{-1}$, when measured at a temperature in the range of from 20 to 30° C. with a diamond ATR cell.

In an embodiment, the invention relates to a crystalline form of LNP023 hydrochloride (Form HB) characterized by having an FTIR spectrum comprising peaks at wavenumbers of (3452±4) cm$^{-1}$, (3274±4) cm$^{-1}$, (2933±4) cm$^{-1}$, (2875±4) cm$^{-1}$, (2732±4) cm$^{-1}$, (1709±4) cm$^{-1}$, (1692±4) cm$^{-1}$, (1658±4) cm$^{-1}$, (1615±4) cm$^{-1}$, (1601±4) cm$^{-1}$, (1515±4) cm$^{-1}$, (1497±4) cm$^{-1}$, (1461±4) cm$^{-1}$, (1439±4) cm$^{-1}$, (1425±4) cm$^{-1}$, (1384±4) cm$^{-1}$, (1243±4) cm$^{-1}$, (1184±4) cm$^{-1}$, (1069±4) cm$^{-1}$, (767±4) cm$^{-1}$ and (739±4) cm$^{-1}$, when measured at a temperature in the range of from 20 to 30° C. with a diamond ATR cell.

In an embodiment, the invention relates to a crystalline form of LNP023 hydrochloride (Form HB) characterized by having an FTIR spectrum comprising peaks at wavenumbers of (3452±4) cm$^{-1}$, (2875±4) cm$^{-1}$, (2732±4) cm$^{-1}$, (1692±4) cm$^{-1}$, (1439±4) cm$^{-1}$, (1243±4) cm$^{-1}$ and (767±4) cm$^{-1}$ and at least one more peak selected from the group consisting of (3274±4) cm$^{-1}$, (2933±4) cm$^{-1}$, (1709±4) cm$^{-1}$, (1658±4) cm$^{-1}$, (1615±4) cm$^{-1}$, (1601±4) cm$^{-1}$, (1515±4) cm$^{-1}$, (1497±4) cm$^{-1}$, (1461±4) cm$^{-1}$, (1425±4) cm$^{-1}$, (1384±4) cm$^{-1}$, (1184±4) cm$^{-1}$, (1069±4) cm$^{-1}$, and (739±4) cm$^{-1}$, when measured at a temperature in the range of from 20 to 30° C. with a diamond ATR cell.

In another embodiment, the invention relates to a crystalline form of LNP023 hydrochloride (Form HB) characterized by having an FTIR spectrum comprising peaks at wavenumbers of:
(3452±2) cm$^{-1}$, (2875±2) cm$^{-1}$, and (1692±2) cm$^{-1}$, or
(3452±2) cm$^{-1}$, (2875±2) cm$^{-1}$, (1692±2) cm$^{-1}$, and (1439±2) cm$^{-1}$; or
(3452±2) cm$^{-1}$, (2875±2) cm$^{-1}$, (1692±2) cm$^{-1}$, (1439±2) cm$^{-1}$ and (1243±2) cm$^{-1}$; or
(3452±2) cm$^{-1}$, (2875±2) cm$^{-1}$, (1692±2) cm$^{-1}$, (1439±2) cm$^{-1}$, (1243±2) cm$^{-1}$ and (767±2) cm$^{-1}$; or
(3452±2) cm$^{-1}$, (2875±2) cm$^{-1}$, (2732±2) cm$^{-1}$, (1692±2) cm$^{-1}$, (1439±2) cm$^{-1}$, (1243±2) cm$^{-1}$ and (767±2) cm$^{-1}$; or
(3452±2) cm$^{-1}$, (2875±2) cm$^{-1}$, (2732±2) cm$^{-1}$, (1709±2) cm$^{-1}$, (1692±2) cm$^{-1}$, (1658±2) cm$^{-1}$, (1439±2) cm$^{-1}$, (1243±2) cm$^{-1}$ and (767±2) cm$^{-1}$; or
(3452±2) cm$^{-1}$, (2875±2) cm$^{-1}$, (2732±2) cm$^{-1}$, (1709±2) cm$^{-1}$, (1692±2) cm$^{-1}$, (1658±2) cm$^{-1}$, (1615±2) cm$^{-1}$, (1439±2) cm$^{-1}$, (1243±2) cm$^{-1}$ and (767±2) cm$^{-1}$; or
(3452±2) cm$^{-1}$, (2875±2) cm$^{-1}$, (2732±2) cm$^{-1}$, (1709±2) cm$^{-1}$, (1692±2) cm$^{-1}$, (1658±2) cm$^{-1}$, (1615±2) cm$^{-1}$, (1601±2) cm$^{-1}$, (1439±2) cm$^{-1}$, (1243±2) cm$^{-1}$ and (767±2) cm$^{-1}$; or
(3452±2) cm$^{-1}$, (2875±2) cm$^{-1}$, (2732±2) cm$^{-1}$, (1709±2) cm$^{-1}$, (1692±2) cm$^{-1}$, (1658±2) cm$^{-1}$, (1615±2) cm$^{-1}$, (1601±2) cm$^{-1}$, (1515±2) cm$^{-1}$, (1439±2) cm$^{-1}$, (1243±2) cm$^{-1}$ and (767±2) cm$^{-1}$; or
(3452±2) cm$^{-1}$, (2875±2) cm$^{-1}$, (2732±2) cm$^{-1}$, (1709±2) cm$^{-1}$, (1692±2) cm$^{-1}$, (1658±2) cm$^{-1}$, (1615±2) cm$^{-1}$, (1601±2) cm$^{-1}$, (1515±2) cm$^{-1}$, (1497±2) cm$^{-1}$, (1439±2) cm$^{-1}$, (1243±2) cm$^{-1}$ and (767±2) cm$^{-1}$; or
(3452±2) cm$^{-1}$, (2875±2) cm$^{-1}$, (2732±2) cm$^{-1}$, (1709±2) cm$^{-1}$, (1692±2) cm$^{-1}$, (1658±2) cm$^{-1}$, (1615±2) cm$^{-1}$, (1601±2) cm$^{-1}$, (1515±2) cm$^{-1}$, (1497±2) cm$^{-1}$, (1461±2) cm$^{-1}$, (1439±2) cm$^{-1}$, (1243±2) cm$^{-1}$ and (767±2) cm$^{-1}$; or
(3452±2) cm$^{-1}$, (2875±2) cm$^{-1}$, (2732±2) cm$^{-1}$, (1709±2) cm$^{-1}$, (1692±2) cm$^{-1}$, (1658±2) cm$^{-1}$, (1615±2) cm$^{-1}$, (1601±2) cm$^{-1}$, (1515±2) cm$^{-1}$, (1497±2) cm$^{-1}$, (1461±2) cm$^{-1}$, (1439±2) cm$^{-1}$, (1425±2) cm$^{-1}$, (1243±2) cm$^{-1}$ and (767±2) cm$^{-1}$; or
(3452±2) cm$^{-1}$, (2875±2) cm$^{-1}$, (2732±2) cm$^{-1}$, (1709±2) cm$^{-1}$, (1692±2) cm$^{-1}$, (1658±2) cm$^{-1}$, (1615±2) cm$^{-1}$, (1601±2) cm$^{-1}$, (1515±2) cm$^{-1}$, (1497±2) cm$^{-1}$, (1461±2) cm$^{-1}$, (1439±2) cm$^{-1}$, (1425±2) cm$^{-1}$, (1384±2) cm$^{-1}$, (1243±2) cm$^{-1}$ and (767±2) cm$^{-1}$; or
(3452±2) cm$^{-1}$, (2875±2) cm$^{-1}$, (2732±2) cm$^{-1}$, (1709±2) cm$^{-1}$, (1692±2) cm$^{-1}$, (1658±2) cm$^{-1}$, (1615±2) cm$^{-1}$, (1601±2) cm$^{-1}$, (1515±2) cm$^{-1}$, (1497±2) cm$^{-1}$, (1461±2) cm$^{-1}$, (1439±2) cm$^{-1}$, (1425±2) cm$^{-1}$, (1384±2) cm$^{-1}$, (1243±2) cm$^{-1}$, (1184±2) cm$^{-1}$ and (767±2) cm$^{-1}$; or
(3452±2) cm$^{-1}$, (2875±2) cm$^{-1}$, (2732±2) cm$^{-1}$, (1709±2) cm$^{-1}$, (1692±2) cm$^{-1}$, (1658±2) cm$^{-1}$, (1615±2) cm$^{-1}$, (1601±2) cm$^{-1}$, (1515±2) cm$^{-1}$, (1497±2) cm$^{-1}$, (1461±2) cm$^{-1}$, (1439±2) cm$^{-1}$, (1425±2) cm$^{-1}$, (1384±2) cm$^{-1}$, (1243±2) cm$^{-1}$, (1184±2) cm$^{-1}$, (1069±2) cm$^{-1}$ and (767±2) cm$^{-1}$; or
(3452±2) cm$^{-1}$, (2875±2) cm$^{-1}$, (2732±2) cm$^{-1}$, (1709±2) cm$^{-1}$, (1692±2) cm$^{-1}$, (1658±2) cm$^{-1}$, (1615±2) cm$^{-1}$, (1601±2) cm$^{-1}$, (1515±2) cm$^{-1}$, (1497±2) cm$^{-1}$, (1461±2) cm$^{-1}$, (1439±2) cm$^{-1}$, (1425±2) cm$^{-1}$, (1384±2) cm$^{-1}$, (1243±2) cm$^{-1}$, (1184±2) cm$^{-1}$, (1069±2) cm$^{-1}$, (767±2) cm$^{-1}$ and (739±2) cm$^{-1}$; or
(3452±2) cm$^{-1}$, (3274±2) cm$^{-1}$, (2875±2) cm$^{-1}$, (2732±2) cm$^{-1}$, (1709±2) cm$^{-1}$, (1692±2) cm$^{-1}$, (1658±2) cm$^{-1}$, (1615±2) cm$^{-1}$, (1601±2) cm$^{-1}$, (1515±2) cm$^{-1}$, (1497±2) cm$^{-1}$, (1461±2) cm$^{-1}$, (1439±2) cm$^{-1}$, (1425±2) cm$^{-1}$, (1384±2) cm$^{-1}$, (1243±2) cm$^{-1}$, (1184±2) cm$^{-1}$, (1069±2) cm$^{-1}$, (767±2) cm$^{-1}$ and (739±2) cm$^{-1}$; or
(3452±2) cm$^{-1}$, (3274±2) cm$^{-1}$, (2933±2) cm$^{-1}$, (2875±2) cm$^{-1}$, (2732±2) cm$^{-1}$, (1709±2) cm$^{-1}$, (1692±2) cm$^{-1}$, (1658±2) cm$^{-1}$, (1615±2) cm$^{-1}$, (1601±2) cm$^{-1}$, (1515±2) cm$^{-1}$, (1497±2) cm$^{-1}$, (1461±2) cm$^{-1}$, (1439±2) cm$^{-1}$, (1425±2) cm$^{-1}$, (1384±2) cm$^{-1}$, (1243±2) cm$^{-1}$, (1184±2) cm$^{-1}$, (1069±2) cm$^{-1}$, (767±2) cm$^{-1}$ and (739±2) cm$^{-1}$, when measured at a temperature in the range of from 20 to 30° C. with a diamond ATR cell.

In an embodiment, the invention relates to a crystalline form of LNP023 hydrochloride (Form HB) characterized by having an FTIR spectrum comprising peaks at wavenumbers of (3452±2) cm$^{-1}$, (2875±2) cm$^{-1}$, (2732±2) cm$^{-1}$, (1692±2) cm$^{-1}$, (1439±2) cm$^{-1}$, (1243±2) cm$^{-1}$, and (767±2) cm$^{-1}$, and at least one more peak selected from the group consisting of (3274±2) cm$^{-1}$, (2933±2) cm$^{-1}$, (1709±2) cm$^{-1}$, (1658±2) cm$^{-1}$, (1615±2) cm$^{-1}$, (1601±2) cm$^{-1}$, (1515±2) cm$^{-1}$, (1497±2) cm$^{-1}$, (1461±2) cm$^{-1}$, (1425±2) cm$^{-1}$, (1384±2) cm$^{-1}$, (1184±2) cm$^{-1}$, (1069±2) cm$^{-1}$, and (739±2) cm$^{-1}$, when measured at a temperature in the range of from 20 to 30° C. with a diamond ATR cell.

Figure 3:
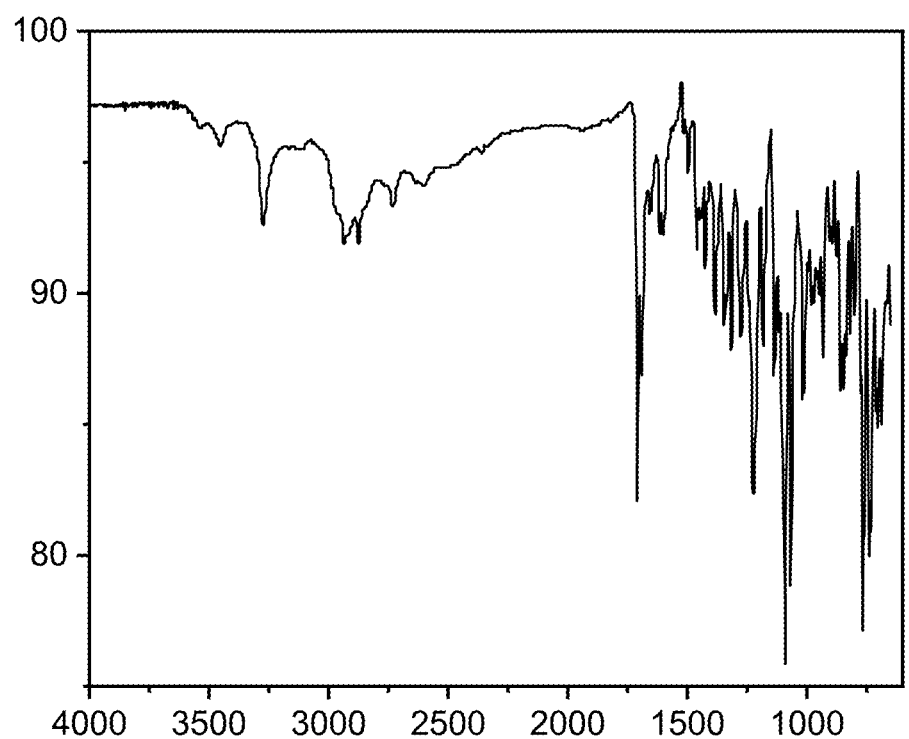
FIG. 3: illustrates a representative FTIR spectrum of Form HB of LNP023 hydrochloride described herein. The x-axis shows the wavenumbers in $cm^{-1}$, the y-axis shows the relative intensity in percent transmittance.

In yet another embodiment, the invention relates to a crystalline form of LNP023 hydrochloride (Form HB) characterized by having an FTIR spectrum essentially the same as shown in FIG. 3 described herein, when measured at a temperature in the range of from 20 to 30° C. with a diamond ATR cell.

Figure 4:
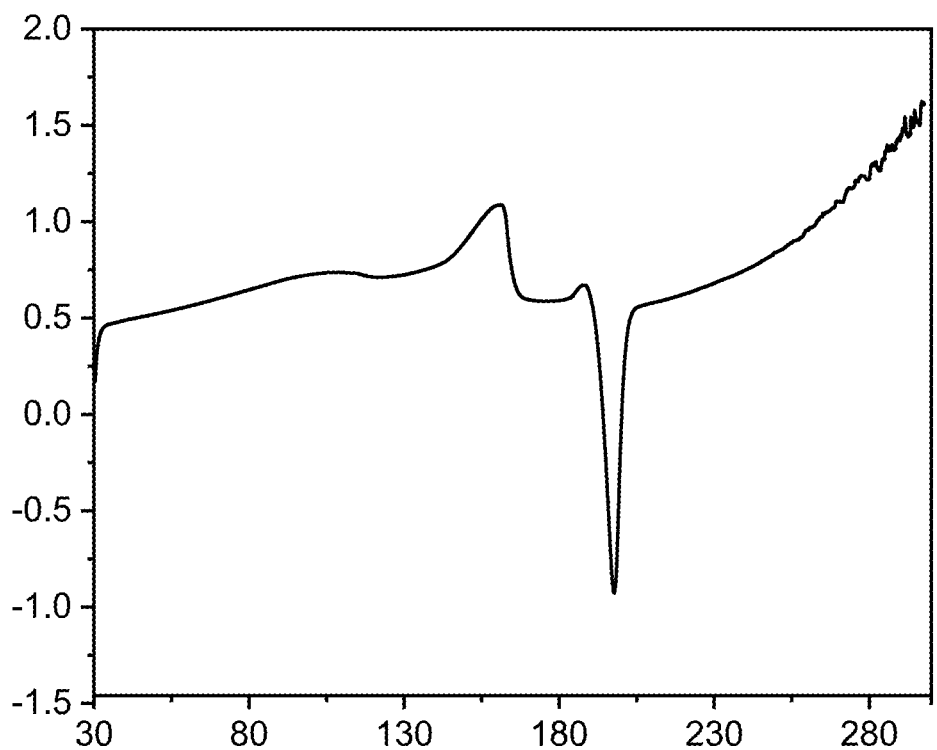
FIG. 4: illustrates a representative DSC curve of Form HB of LNP023 hydrochloride described herein. The x-axis shows the temperature in degree Celsius (° C.), the y-axis shows the heat flow rate in Watt per gram (W/g) with endothermic peaks going up.

Exemplification of DSC Embodiments:

In an embodiment, LNP023 hydrochloride (Form HB) can be characterized by having a DSC profile essentially the same as shown in in FIG. 4. In an embodiment, the invention relates to a crystalline form of LNP023 hydrochloride (Form HB) characterized by having a DSC curve showing a broad endothermic event which ends at about 170° C., followed by exothermic decomposition at about 200° C., when measured at a heating rate of 10 K/min. In an embodiment, the broad endothermic event which ends at about 170° C., is an endothermic event in the range of 35° C. to 170° C. when measured at a heating rate of 10 K/min.

Figure 5:
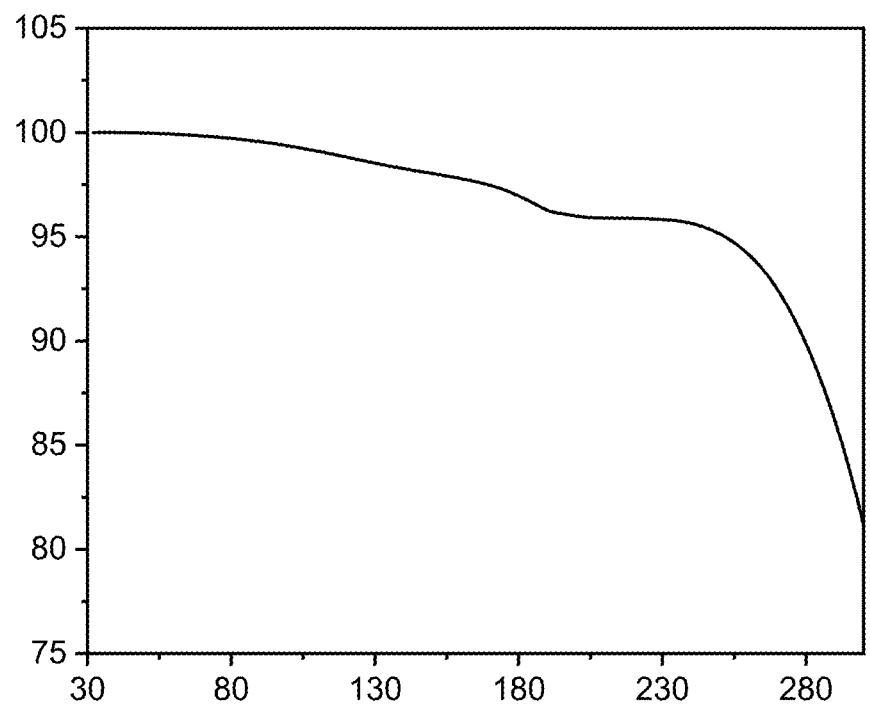
FIG. 5: illustrates a representative TGA curve of Form HB of LNP023 hydrochloride described herein. The x-axis shows the temperature in degree Celsius (° C.), the y-axis shows the mass (loss) of the sample in weight percent (w-%).

Exemplification of TGA Embodiments:

In an embodiment, LNP023 hydrochloride (Form HB) can be characterized by a thermal gravimetric analysis (TGA) essentially the same as shown in FIG. 5. In an embodiment, the invention relates to a crystalline form of LNP023 hydrochloride (Form HB) characterized by having a TGA curve showing a mass loss at about 220° C., such as at a temperature of from 200 to 220° C., due to loss of water and residual solvents of not more than 4.5 w-%, e.g., of not more than 4.3 w-%, e.g., of not more than 4.0 w-%, e.g., of not more than 3.8 w-%, for example of not more than 3.4 w-%, based on the weight of the crystalline form, when heated from 30 to 300° C. at a rate of 20 K/min.

Figure 6:
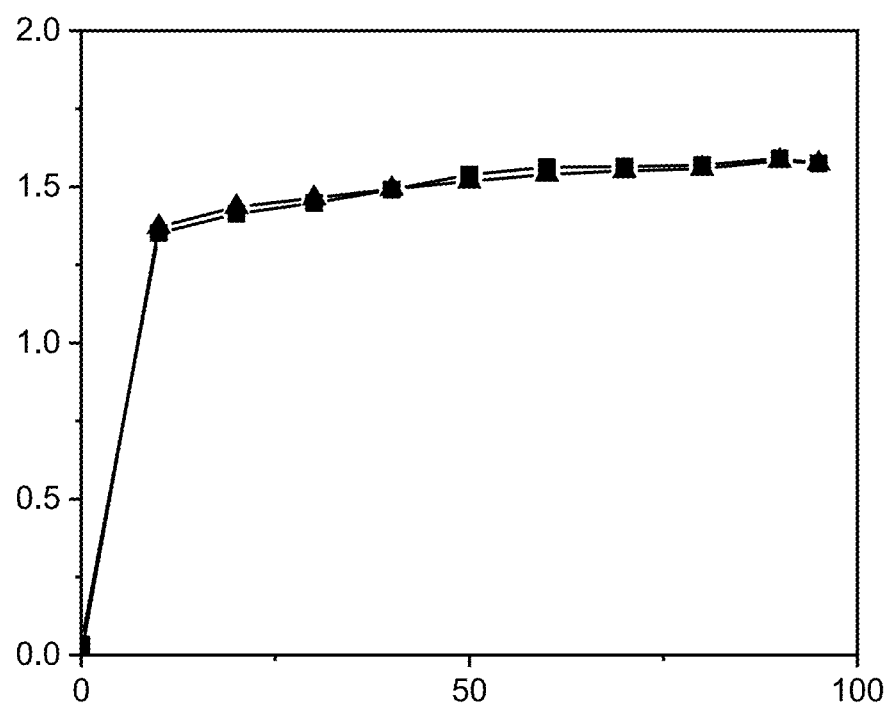
FIG. 6: illustrates representative DVS isotherms of Form HB of LNP023 hydrochloride described herein in the range of from 0 to 95% relative humidity. The x-axis displays the relative humidity in percent (%) measured at a temperature of (25.0±1.0)° C., the y-axis displays the equilibrium mass change in weight percent (w-%) in respect to the sample weight at 0% RH. The sorption cycle is marked by triangles, whereas the desorption cycle is marked by squares.

Exemplification of DVS Embodiments:

In an embodiment, LNP023 hydrochloride (Form HB) can be characterized by a DVS essentially the same as shown in FIG. 6. In an embodiment, the invention relates to a crystalline form of LNP023 hydrochloride (Form HB) characterized by showing a mass change of not more than 4.5 w-%, e.g., of not more than 4.0 w-%, e.g., of not more than 3.0 w-%, e.g., of not more than 2.0 w-%, for example of not more than 1.8 w %, 1.6 w-%, 1.5 w-% or 1.4 w-%, based on the weight of the crystalline form, when measured with DVS at a relative humidity in the range of from 0 to 95% and a temperature of $(25\pm1.0°)$ C.

Exemplification of Further Embodiments:

In another embodiment, the invention relates to a crystalline form of LNP023 hydrochloride (Form HB) characterized as being a non-solvated form. In an embodiment, the crystalline form of LNP023 hydrochloride is in a hydrated form, for example, the monohydrate form.

Exemplification of Morphology

In an embodiment, the invention relates to a crystalline form of LNP023 hydrochloride (Form HB) characterized by exhibiting columnar or equant-like morphology.

In an embodiment, the invention relates to a crystalline form of LNP023 hydrochloride (Form HB) having a crystal habit which is essentially equant or columnar, e.g., essentially equant, in shape. This leads to preferred bulk and flow properties as opposed to small acicular (needle) or lath (blade) shaped crystals. Such preferred crystal shapes can be obtained by performing the process as set out herein, for example, when performing crystallization engineering techniques including temperature cycling followed by milling leading to a reduction in particle size.

The resulting particles are characterized by a suitable aspect ratio. The aspect ratio $\psi_A$ ($0<\psi_A\leq 1$) is defined by the ratio of the minimum to the maximum Feret diameter $\psi A = x_{Feret\ min}/x_{Feret\ max}$. It gives an indication for the elongation of the particle, i.e. the smaller the value, the more elongated is the particle. Therefore, in additional embodiments, the equant-shaped particles of the crystalline form of LNP023 hydrochloride (Form HB) have an aspect ratio (a50) of above about 0.4 such as above about 0.45. In other embodiments, the equant-shaped particles of Form HB have an aspect ratio from about 0.4 to about 0.7, for example from about 0.45 to 0.6.

In further embodiments, the particle size distribution $X_{90}$ of the equant-shaped particles of the crystalline form of LNP023 hydrochloride (Form HB) is less than about 300 µm, such as less than about 200 µm, for example, less than about 150 µm. In further embodiments, the particle size distribution $X_{90}$ is from about 30 to about 150 µm, such as from about 35 to about 130 µm, for example, from about 40 to about 105 µm.

In additional embodiments, the particle size distribution $X_{50}$ of the equant-shaped particles of Form HB is from about 5 to about 100 µm, such as from about 10 to about 70 µm, for example, from about 15 to about 55 µm.

In yet further embodiments, the particle size distribution $X_{10}$ of the equant-shaped particles of Form HB is from about 0.1 to about 50 µm, such as from about 1 to about 30 µm, for example, from about 2 to about 20 µm.

In a further embodiment, the equant-shaped particles of Form HB have a consolidated (15 kPa) bulk density of less than about 0.8 g/ml, such as less than about 0.7 g/ml. In other embodiments, the equant-shaped particles of Form HB have a consolidated (15 kPa) bulk density from about 0.4 to about 0.7 g/ml, such as from about 0.50 to about 0.65 g/ml, for example, from about 0.55 to about 0.60 g/ml.

Composition

Exemplifications of Embodiments:

In another aspect, the invention relates to a composition comprising the Form HB of LNP023 hydrochloride described herein as defined in any one of the embodiments described above, said composition being essentially free of any other solid form of LNP023 hydrochloride. For example, a composition comprising the Form HB of LNP023 hydrochloride described herein comprises at most 20 w-%, e.g., at most 10 w-%, e.g., at most 5, 4, 3, 2 or 1 w-% of any other solid form of LNP023 hydrochloride, based on the weight of the composition. In an embodiment, the any other solid form of LNP023 hydrochloride is Form A of WO 2015/009616 or amorphous. Form A of LNP023 hydrochloride exhibits a PXRD comprising amongst others a characteristic peak at 2-Theta angles of $(11.6\pm0.1)°$, when measured at a temperature in the range of from 20 to 30° C. with Cu-Kalpha$_{1,2}$ radiation having a wavelength of 0.15419 nm. Therefore, the absence of this peak at 2-Theta angles of $(11.6\pm0.1)°$ in the PXRD confirms the absence of Form A of LNP023 hydrochloride in the composition.

In an embodiment, the invention relates to a composition comprising the Form HB of LNP023 hydrochloride described herein as defined in any one of the embodiments described above, said composition having a PXRD comprising no peak at 2-Theta angles of $(11.6\pm0.1)°$, when measured at a temperature in the range of from 20 to 30° C. with Cu-Kalpha$_{1,2}$ radiation having a wavelength of 0.15419 nm.

In an embodiment, the invention relates to a composition comprising at least 90 w-%, including at least 90, 91, 92, 93, 94, 95, 96, 97, 98 and 99 w-%, and also including equal to about 100 w-% of the crystalline Form HB of LNP023 hydrochloride as defined in any one of the embodiments described above, based on the total weight of the composition. The remaining material may comprise other solid form(s) of LNP023 hydrochloride, or reaction impurities, or processing impurities arising from the preparation of the composition.

Process

Exemplifications of Embodiments:

In another aspect, the invention relates to a process for the preparation of Form HB of LNP023 hydrochloride described herein or the composition comprising the same as defined in any one of the aspects and their corresponding embodiments described above comprising:
(i) providing LNP023 hydrochloride in solid form;
(ii) suspending LNP023 hydrochloride provided in step (i) in a first solvent comprising acetone and water and heating to dissolve the solid, to provide a solution;
(iii) cooling the solution obtained in step (ii) and adding a second solvent comprising acetone, or ethyl acetate, or a combination thereof, to provide crystals in a mother liquor;
(iv) separating at least a part of the crystals obtained in step (iii) from the mother liquor;
(v) optionally washing the isolated crystals obtained in step (iv); and
(vi) drying the crystals obtained in step (iv) or (v).

Exemplification of Process Description:

The solid LNP023 hydrochloride starting material can be prepared according to the procedure disclosed in Example 26d of WO 2015/009616.

The solid starting material provided in step (i) can be suspended in a first solvent comprising acetone and water. The first solvent may comprise additional organic solvents. In an embodiment, acetone and water can be the only solvents present in the suspension. The LNP023 hydrochloride concentration of the suspension is, e.g., in the range of from about 0.07 to 0.30 g/g, e.g., from about 0.10 to 0.25 g/g, e.g., from about 0.15 to 0.20 g/g, for example the concentration is about 0.20 g/g. In an embodiment, the ratio of acetone to water (g/g) is, e.g., 60:40 to 90:10, such as 65:45 to 85:15, e.g., 75:25 to 80:20. In an embodiment, heating in step (ii) can be performed at elevated temperature, for example, at a temperature in the range of from about 30 to 56° C., e.g., from about 45 to 55° C. Heating can be accompanied by any kind of movement of the solid material suspended in the solvent including, but not limited to e.g. agitation, stirring, mixing, shaking, vibration, sonication, wet milling and the like. Once the solid material has been dissolved, the solution can be cooled down to a temperature in the range of from about 20 to 50° C., e.g., from about 35 to 45° C., and a second solvent comprising acetone, ethyl acetate, or a combination thereof, can be added. The second solvent may comprise additional organic solvents or water. In an embodiment, acetone and ethyl acetate can be the only solvents added in step (iii). If both acetone and ethyl acetate are used as the second solvent, they can be added as a solvent mixture of acetone and ethyl acetate or they can be added consecutively. In an embodiment, when added consecutively, acetone is added first followed by ethyl acetate. The LNP023 hydrochloride concentration is, e.g., in the range of from about 0.04 to 0.15 g/g, e.g., from about 0.05 to 0.10 g/g, and e.g., from about 0.05 to 0.07 g/g, for example the concentration is about 0.06 g/g. The ratio of acetone to ethyl acetate (g/g) is, e.g., 0.5:3 to 1:1, such as 1:2. In an embodiment, the suspension can be further cooled down to a temperature in the range of from about 0 to 25° C., e.g., from about 5 to 15° C., e.g., 10° C. to complete crystallization. Once, Form HB is obtained in essentially pure form, at least a part of the crystals can be separated from the mother liquor. In an embodiment, the crystals can be separated from their mother liquor by any conventional method such as filtration, centrifugation, solvent evaporation or decantation, e.g., by filtration or centrifugation. In an embodiment, the crystals can be separated from their mother liquor by filtration.

Optionally, in a further step the isolated crystals can be washed with a suitable solvent, for example an organic solvent or water. Suitable organic solvents comprise but are not limited to acetone and ethyl acetate.

The obtained crystals can then be dried. Drying may be performed at a temperature of about 70° C. or less, e.g., of about 60° C. or less, e.g., of about 50° C. Drying can also be performed at about room temperature. Drying may be performed for a period in the range of from about 2 to 24 hours, e.g., from about 4 to 16 hours, e.g., from about 6 to 10 hours. In an embodiment, drying may be performed for a period of from about 6 to 8 hours. Drying may be performed at ambient pressure or under reduced pressure. In an embodiment, drying is performed at a pressure of about 200 mbar or less, e.g., of about 150 mbar or less. In an embodiment, drying is performed at a pressure of about 80 mbar or less. In an embodiment, drying is performed, for example, under vacuum of about 50 mbar or less.

In an embodiment, certain crystallization techniques can be applied to the process to obtain Form HB crystals with improved product processability. The techniques include but are not limited to, temperature cycling or adding the second solvent over an extended period of time, such as over 12 to 36 h, e.g., can be temperature cycling. Temperature cycling can be conducted as follows: In step (iii) before a second solvent is added, the solution can be cooled down to a temperature in the range of from about 0 to 25° C., e.g., from about 5 to 15° C., e.g., 10° C., and then can be heated up to a temperature in the range of from about 30 to 45° C., e.g., from about 30 to 40° C., e.g., 35° C. This temperature cycle can be performed for at least 3 times, e.g., for at least 6 times, e.g., for at least 8 times, such as 6 to 12 times. After the temperature cycling, a second solvent can be added. In an embodiment, the second solvent can be ethyl acetate.

Form HB after being engineered, i.e. after applying certain crystallization techniques as described above, consists of crystals with well-defined morphology, said morphology leading to excellent powder properties and processability allowing the formulation of a drug product comprising Form HB via standard manufacturing processes and equipment. In an embodiment, in contrast to Form A, which cannot be engineered in such a manner, Form HB is not brittle so that issues with milling and a broad particle size distribution can be minimized. In addition, the flow properties of Form HB are superior over Form A. Hence, Form HB, particularly when being engineered, combines high physicochemical stability with excellent powder properties. It is therefore superior to Form A and is the ideal solid state form of LNP023 hydrochloride for the standard manufacturing of an improved pharmaceutical composition.

In an embodiment, the invention relates to a process for the preparation of Form HB of LNP023 hydrochloride described herein, or the composition comprising the same as defined in any one of the aspects and their corresponding embodiments described above comprising as step (iii) of the procedure described above:
  a) cooling the solution obtained in step (ii) followed by re-heating the solution again;
  b) repeating step (a) at least 3 times; and
  c) adding a second solvent comprising acetone, ethyl acetate, or a combination thereof.

Exemplification of Milling

Before the particles of the Form HB of LNP023 hydrochloride described herein are filled into capsules or are otherwise further processed, they are, e.g., milled. Milling can be conducted to enable easy filling of the particles directly into the capsules, particularly without the need of further excipients.

In an embodiment, the particle size of Form HB of LNP023 hydrochloride is reduced by using rotor impact milling. Rotor impact milling can be performed by using different static and rotating tooling elements, e.g. rotating wing beater with static screen, rotating wing beater with static screen and impact element, rotating pin disc with static pin disc, or rotating pin disc with rotating pin disc. Form HB of LNP023 hydrochloride that is to be milled is transported into the rotor impact mill by appropriate powder transport systems, e.g. vibratory feeder, or double screw feeder, for adequate control of related powder feed rate. The powder is further transported to the impact tooling elements by a gas flow, either generated by the rotating elements of the rotor impact mill or by a blower connected with the rotor impact mill. Particle size reduction of Form HB of LNP023 hydrochloride particles takes place by impact at the rotating elements, by impact at the static elements, or by impact between colliding Form HB particles. Adequate process parameters like rotor speed and feed rate for tailored Form HB of LNP023 hydrochloride physical properties are related to the specific equipment parameters of the rotor impact mill. The milled product with tailored physical properties is collected in a product container after separation from transport gas by, e.g. filters, cyclones. The milled product may be finally blended by appropriate techniques, e.g. diffusion blender, to obtain appropriate physical homogeneity of a manufactured batch.

Rotor impact milling may be performed, for example, by rotor impact milling using rotating a pin disc with static pin disc tooling, often described in the art as a pin mill. Scale independent parameters for rotor speed and feed rate, can be described by rotor tip speed and specific feed rate. The rotor speed of a specific equipment scale is in principle connected with the pin disc diameter of the related equipment scale by parameter rotor tip speed for a scale independent parameter. The feed rate of a specific equipment scale is in principle related to pin surface area of the related equipment scale by parameter specific feed rate for a scale independent parameter. Form HB of LNP023 hydrochloride product with tailored physical properties can be obtained with rotor impact milling with the following scale independent milling parameters: a rotor tip speed from 10 to 60 m/s, whereas the diameter of the outer rotating pins is considered for normalization, or a specific feed rate up to about 4,000 kg/(h·m$^2$), whereas the cylindrical pin surface area of rotating pins is considered for normalization.

In a scale dependent example, Form HB of LNP023 hydrochloride can be milled by using a rotor impact mill, such as model 100 UPZ, Hosokawa Alpine AG, Augsburg/Germany, and a rotating pin disc with static pin disc tooling, often described as a pin mill in the public domain. The product with tailored physical properties can be obtained by operating the process with a rotor speed from F800 to 10,500 rpm, e.g., from 4,000 to 8,500 rpm, e.g., at a rotor speed of 6,000 rpm. The feed rate is, e.g., from 1 to 22 kg/h, e.g., from 6 to 18 kg/h, e.g., at a feed rate of 15 kg/h.

Pharmaceutical Compositions and Use
Exemplifications of Embodiments:

In a further aspect, the invention relates to the use of Form HB of LNP023 hydrochloride described herein or the composition comprising Form HB of LNP023 hydrochloride as defined in any one of the aspects and their corresponding embodiments described above for the preparation of a pharmaceutical composition.

In yet another aspect, the invention relates to a pharmaceutical composition comprising Form HB of LNP023 hydrochloride or the composition comprising Form HB of LNP023 hydrochloride as defined in any one of the aspects and their corresponding embodiments described above, e.g., in a predetermined or therapeutically effective amount, and at least one pharmaceutically acceptable excipient.

In an embodiment, the pharmaceutical composition comprising Form HB of LNP023 hydrochloride as defined in any one of the aspects and their corresponding embodiments described above, comprises LNP023 hydrochloride at a dose of up to about 200 mg, calculated as the anhydrous LNP023 free base.

In an embodiment thereof, the pharmaceutical composition comprises LNP023 hydrochloride at a dose of from about 10 mg to about 200 mg, calculated as the anhydrous LNP023 free base.

In an embodiment thereof, the pharmaceutical composition comprises LNP023 hydrochloride at a dose of about 10 mg, about 25 mg, about 50 mg, about 100 mg, or about 200 mg, each calculated as the anhydrous LNP023 free base.

In an embodiment thereof, the pharmaceutical composition comprises LNP023 hydrochloride at a dose of 10 mg, 25 mg, 50 mg, 100 mg, or 200 mg, each calculated as the anhydrous LNP023 free base.

In an embodiment, the therapeutically effective amount of Form HB of LNP023 hydrochloride is selected from the group consisting of 1, 5, 10, 25, 50, 100 and 200 mg, calculated as anhydrous LNP023 free base. In an embodiment, the therapeutically effective amount of Form HB of LNP023 hydrochloride is 100 or 200 mg. In an embodiment, the therapeutically effective amount of Form HB of LNP023 hydrochloride is 50 mg. In an embodiment, the therapeutically effective amount of Form HB of LNP023 hydrochloride is 10 mg.

At least one pharmaceutically acceptable excipient, which may be comprised in a pharmaceutical composition described herein, is, e.g., selected from the group consisting of vehicles, fillers, diluents, binders, disintegrants, lubricants, glidants and combinations thereof. Suitable vehicles are for example a dispersing liquid or a capsule. In one preferred embodiment, the pharmaceutical composition comprises one pharmaceutically acceptable excipient, for example, a vehicle.

In a preferred embodiment, the pharmaceutical composition comprising Form HB of LNP023 hydrochloride or the composition comprising Form HB of LNP023 hydrochloride as defined in any one of the aspects and their corresponding embodiments described above is an oral solid dosage form. In an embodiment, the oral solid dosage form is selected from the group consisting of tablets and capsules. In an embodiment, the oral dosage form is in the form of a tablet. In an embodiment, the oral dosage form is a capsule. In an embodiment, the capsule is in a size 0 capsule.

The tablet may be prepared by mixing the Form HB of LNP023 hydrochloride or the composition comprising Form HB of LNP023 hydrochloride as defined in any one of the aspects and their corresponding embodiments described above with at least one excipient such as fillers, diluents, binders, disintegrants, lubricants, glidants or combinations thereof. Optionally, a granulation step such as a dry or wet granulation step is performed before compression.

The capsule may be prepared by mixing Form HB of LNP023 hydrochloride or the composition comprising Form HB of LNP023 hydrochloride as defined in any one of the aspects and their corresponding embodiments described above with at least one excipient such as fillers, diluents, binders, disintegrants, lubricants, glidants or combinations thereof and filling the blend into a capsule which is used as the vehicle. Alternatively Form HB of LNP023 hydrochloride is filled neat into the capsule which is used as the vehicle. The capsule shell may be a gelatin shell or a hydroxypropylmethylcellulose (HPMC) shell.

In an embodiment, the invention relates to a pharmaceutical composition comprising Form HB of LNP023 hydrochloride particles in a capsule, such as a size 0 capsule. In an embodiment, the Form HB particles in the capsule have aspect ratio between from 0.4 to about 0.7, such as from 0.45 to 0.6. In an embodiment, the Form HB particles in the capsule have particle size distribution $X_{50}$ of from about 5 to about 100 µm, such as from about 10 to about 70 µm, for example, from about 15 to about 55 µm. In an embodiment, the Form HB particles in the capsule have a consolidated (15 kPa) bulk density from about 0.4 to about 0.7 g/ml, such as from about 0.50 to about 0.65 g/ml, for example, from about 0.55 to about 0.60 g/ml.

In a further aspect, the invention relates to Form HB of LNP023 hydrochloride or the composition comprising Form HB of LNP023 hydrochloride or the pharmaceutical composition comprising the same as defined in any one of the above described aspects and their corresponding embodiments for use in the treatment of the diseases and disorders described herein.

In yet another aspect, the invention relates to Form HB of LNP023 hydrochloride or the composition comprising Form HB of LNP023 hydrochloride or the pharmaceutical composition comprising the same as defined in any one of the above described aspects and their corresponding embodiments for use in the treatment or prophylaxis of the indications disclosed in WO 2015/009616 and WO 2019/043609, specifically in the treatment or prophylaxis of paroxysmal nocturnal hemoglobinuria (PNH), of the complement-driven renal diseases C3G (C3 glomerulopathy), IgAN (immunoglobuline A nephropathy) and other nephropathies with evidence of glomerular C3 deposition such as MN (membranous nephropathy) and HUS (*E. coli* induced hemolytic uremic syndrome) as well as atypically hemolytic uremic syndrome (aHUS).

In another aspect, the invention relates to a method of treating the diseases and disorders disclosed in WO 2015/009616 and WO 2019/043609, each of which is incorporated herein by reference in its entirety, in a subject in need thereof. In an embodiment, the disease or disorder is selected from paroxysmal nocturnal hemoglobinuria (PNH), of the complement-driven renal diseases C3G (C3 glomerulopathy), IgAN (immunoglobuline A nephropathy) and other nephropathies with evidence of glomerular C3 deposition, such as MN (membranous nephropathy) and HUS (*E. coli* induced hemolytic uremic syndrome), as well as atypically hemolytic uremic syndrome (aHUS). In an embodiment, the method comprises administering to the subject a therapeutically effective amount of Form HB of LNP023 hydrochloride as described herein.

In another aspect, the invention relates to a method of treating paroxysmal nocturnal hemoglobinuria (PNH) in a subject in need thereof, the method comprising administering a therapeutically effective amount of Form HB of LNP023 to the subject, to thereby treat the subject.

In an embodiment, the method of treating PNH in the subject comprises administering Form HB of LNP023 to the subject at a daily dose of up to about 400 mg, calculated as the anhydrous LNP023 free base. In an embodiment, the administration is a twice daily (b.i.d.), e.g., about every 12 hours, dose of up to about 200 mg, calculated as the anhydrous LNP023 free base.

In an embodiment, the method of treating PNH in the subject comprises administering Form HB of LNP023 to the subject at a daily dose of about 20 mg to about 400 mg, calculated as the anhydrous LNP023 free base. In an embodiment, the administration is twice daily (b.i.d.), e.g., about every 12 hours, of a dose of about 10 mg to about 200 mg, calculated as the anhydrous LNP023 free base.

In an embodiment, the method of treating PNH in the subject comprises administering Form HB of LNP023 to the subject at a daily dose of about 20 mg, about 50 mg, about 100 mg, about 200 mg, or about 400 mg, calculated as the anhydrous LNP023 free base. In an embodiment, the administration is a twice daily (b.i.d.), e.g., about every 12 hours, dose of about 10 mg, about 25 mg, about 50 mg, about 100 mg, or about 200 mg, calculated as the anhydrous LNP023 free base.

In an embodiment of the method of treating PNH, Form HB of LNP023 is administered to the subject at a daily total dose of about 20 mg, calculated as the anhydrous LNP023 free base. In an embodiment, the administration is twice daily (b.i.d.), e.g., about every 12 hours, of a dose of about 10 mg.

In an embodiment of the method of treating PNH, Form HB of LNP023 is administered to the subject at a daily total dose of about 50 mg, calculated as the anhydrous LNP023 free base. In an embodiment, the administration is twice daily (b.i.d.), e.g., about every 12 hours, of a dose of about 25 mg.

In an embodiment of the method of treating PNH, Form HB of LNP023 is administered to the subject at a daily total dose of about 100 mg, calculated as the anhydrous LNP023 free base. In an embodiment, the administration is twice daily (b.i.d.), e.g., about every 12 hours, of a dose of about 50 mg.

In an embodiment of the method of treating PNH, Form HB of LNP023 is administered to the subject at a daily total dose of about 200 mg, calculated as the anhydrous LNP023 free base. In an embodiment, the administration is twice daily (b.i.d.), e.g., about every 12 hours, of a dose of about 100 mg.

In an embodiment of the method of treating PNH, Form HB of LNP023 is administered to the subject at a daily total dose of about 400 mg, calculated as the anhydrous LNP023 free base. In an embodiment, the administration is twice daily (b.i.d.), e.g., about every 12 hours, of a dose of about 200 mg.

In an embodiment of the method of treating PNH, Form HB of LNP023 is administered orally to the subject twice daily (b.i.d.), e.g., about every 12 hours.

In an embodiment of the method of treating PNH, Form HB of LNP023 is administered orally twice daily (b.i.d.), e.g., about every 12 hours, to the subject at a dose of 200 mg, calculated as the anhydrous LNP023 free base.

In another aspect, the invention relates to a method of treating complement-driven renal diseases C3G (C3 glomerulopathy) in a subject in need thereof, the method comprising administering a therapeutically effective amount of Form HB of LNP023 to the subject, to thereby treat the subject.

In an embodiment, the method of treating C3G in the subject comprises administering Form HB of LNP023 to the subject at a daily dose of up to about 400 mg, calculated as the anhydrous LNP023 free base. In an embodiment, the administration is a twice daily (b.i.d.), e.g., about every 12 hours, dose of up to about 200 mg, calculated as the anhydrous LNP023 free base.

In an embodiment, the method of treating C3G in the subject comprises administering Form HB of LNP023 to the subject at a daily dose of about 20 mg to about 400 mg, calculated as the anhydrous LNP023 free base. In an embodiment, the administration is twice daily (b.i.d.), e.g., about every 12 hours, of a dose of about 10 mg to about 200 mg, calculated as the anhydrous LNP023 free base.

In an embodiment, the method of treating C3G in the subject comprises administering Form HB of LNP023 to the subject at a daily dose of about 20 mg, about 50 mg, about 100 mg, about 200 mg, or about 400 mg, calculated as the anhydrous LNP023 free base. In an embodiment, the administration is a twice daily (b.i.d.), e.g., about every 12 hours, dose of about 10 mg, about 25 mg, about 50 mg, about 100 mg, or about 200 mg, calculated as the anhydrous LNP023 free base.

In an embodiment of the method of treating C3G, Form HB of LNP023 is administered to the subject at a daily total dose of about 20 mg, calculated as the anhydrous LNP023 free base. In an embodiment, the administration is twice daily (b.i.d.), e.g., about every 12 hours, of a dose of about 10 mg.

In an embodiment of the method of treating C3G, Form HB of LNP023 is administered to the subject at a daily total dose of about 50 mg, calculated as the anhydrous LNP023 free base. In an embodiment, the administration is twice daily (b.i.d.), e.g., about every 12 hours, of a dose of about 25 mg.

In an embodiment of the method of treating C3G, Form HB of LNP023 is administered to the subject at a daily total dose of about 100 mg, calculated as the anhydrous LNP023 free base. In an embodiment, the administration is twice daily (b.i.d.), e.g., about every 12 hours, of a dose of about 50 mg.

In an embodiment of the method of treating C3G, Form HB of LNP023 is administered to the subject at a daily total dose of about 200 mg, calculated as the anhydrous LNP023 free base. In an embodiment, the administration is twice daily (b.i.d.), e.g., about every 12 hours, of a dose of about 100 mg.

In an embodiment of the method of treating C3G, Form HB of LNP023 is administered to the subject at a daily total dose of about 400 mg, calculated as the anhydrous LNP023 free base. In an embodiment, the administration is twice daily (b.i.d.), e.g., about every 12 hours, of a dose of about 200 mg.

In an embodiment of the method of treating C3G, Form HB of LNP023 is administered orally to the subject twice daily (b.i.d.), e.g., about every 12 hours.

In an embodiment of the method of treating C3G, Form HB of LNP023 is administered orally twice daily (b.i.d.), e.g., about every 12 hours, to the subject at a dose of 200 mg, calculated as the anhydrous LNP023 free base.

In another aspect, the invention relates to a method of treating IgAN (immunoglobuline A nephropathy) in a subject in need thereof, the method comprising administering a therapeutically effective amount of Form HB of LNP023 to the subject, to thereby treat the subject.

In an embodiment, the method of treating IgAN in the subject comprises administering Form HB of LNP023 to the subject at a daily dose of up to about 400 mg, calculated as the anhydrous LNP023 free base. In an embodiment, the administration is a twice daily (b.i.d.), e.g., about every 12 hours, dose of up to about 200 mg, calculated as the anhydrous LNP023 free base.

In an embodiment, the method of treating IgAN in the subject comprises administering Form HB of LNP023 to the subject at a daily dose of about 20 mg to about 400 mg, calculated as the anhydrous LNP023 free base. In an embodiment, the administration is twice daily (b.i.d.), e.g., about every 12 hours, of a dose of about 10 mg to about 200 mg, calculated as the anhydrous LNP023 free base.

In an embodiment, the method of treating IgAN in the subject comprises administering Form HB of LNP023 to the subject at a daily dose of about 20 mg, about 50 mg, about 100 mg, about 200 mg, or about 400 mg, calculated as the anhydrous LNP023 free base. In an embodiment, the administration is a twice daily (b.i.d.), e.g., about every 12 hours, dose of about 10 mg, about 25 mg, about 50 mg, about 100 mg, or about 200 mg, calculated as the anhydrous LNP023 free base.

In an embodiment of the method of treating IgAN, Form HB of LNP023 is administered to the subject at a daily total dose of about 20 mg, calculated as the anhydrous LNP023 free base. In an embodiment, the administration is twice daily (b.i.d.), e.g., about every 12 hours, of a dose of about 10 mg.

In an embodiment of the method of treating IgAN, Form HB of LNP023 is administered to the subject at a daily total dose of about 50 mg, calculated as the anhydrous LNP023 free base. In an embodiment, the administration is twice daily (b.i.d.), e.g., about every 12 hours, of a dose of about 25 mg.

In an embodiment of the method of treating IgAN, Form HB of LNP023 is administered to the subject at a daily total dose of about 100 mg, calculated as the anhydrous LNP023 free base. In an embodiment, the administration is twice daily (b.i.d.), e.g., about every 12 hours, of a dose of about 50 mg.

In an embodiment of the method of treating IgAN, Form HB of LNP023 is administered to the subject at a daily total dose of about 200 mg, calculated as the anhydrous LNP023 free base. In an embodiment, the administration is twice daily (b.i.d.), e.g., about every 12 hours, of a dose of about 100 mg.

In an embodiment of the method of treating IgAN, Form HB of LNP023 is administered to the subject at a daily total dose of about 400 mg, calculated as the anhydrous LNP023 free base. In an embodiment, the administration is twice daily (b.i.d.), e.g., about every 12 hours, of a dose of about 200 mg.

In an embodiment of the method of treating IgAN, Form HB of LNP023 is administered orally to the subject twice daily (b.i.d.), e.g., about every 12 hours.

In an embodiment of the method of treating IgAN, Form HB of LNP023 is administered orally twice daily (b.i.d.), e.g., about every 12 hours, to the subject at a dose of 200 mg, calculated as the anhydrous LNP023 free base.

In another aspect, the invention relates to a method of treating MN (membranous nephropathy), e.g., idiopathic MN (iMN), in a subject in need thereof, the method comprising administering a therapeutically effective amount of Form HB of LNP023 to the subject, to thereby treat the subject.

In an embodiment, the method of treating MN, e.g., iMN, in the subject comprises administering Form HB of LNP023 to the subject at a daily dose of up to about 400 mg, calculated as the anhydrous LNP023 free base. In an embodiment, the administration is a twice daily (b.i.d.), e.g., about every 12 hours, dose of up to about 200 mg, calculated as the anhydrous LNP023 free base.

In an embodiment, the method of treating MN, e.g., iMN, in the subject comprises administering Form HB of LNP023 to the subject at a daily dose of about 20 mg to about 400 mg, calculated as the anhydrous LNP023 free base. In an embodiment, the administration is twice daily (b.i.d.), e.g., about every 12 hours, of a dose of about 10 mg to about 200 mg, calculated as the anhydrous LNP023 free base.

In an embodiment, the method of treating MN, e.g., iMN, in the subject comprises administering Form HB of LNP023 to the subject at a daily dose of about 20 mg, about 50 mg, about 100 mg, about 200 mg, or about 400 mg, calculated as the anhydrous LNP023 free base.

In an embodiment, the administration is a twice daily (b.i.d.), e.g., about every 12 hours, dose of about 10 mg, about 25 mg, about 50 mg, about 100 mg, or about 200 mg, calculated as the anhydrous LNP023 free base.

In an embodiment of the method of treating MN, Form HB of LNP023 is administered to the subject at a daily total dose of about 20 mg, calculated as the anhydrous LNP023 free base. In an embodiment, the administration is twice daily (b.i.d.), e.g., about every 12 hours, of a dose of about 10 mg.

In an embodiment of the method of treating MN, Form HB of LNP023 is administered to the subject at a daily total dose of about 50 mg, calculated as the anhydrous LNP023 free base. In an embodiment, the administration is twice daily (b.i.d.), e.g., about every 12 hours, of a dose of about 25 mg.

In an embodiment of the method of treating MN, Form HB of LNP023 is administered to the subject at a daily total dose of about 100 mg, calculated as the anhydrous LNP023 free base. In an embodiment, the administration is twice daily (b.i.d.), e.g., about every 12 hours, of a dose of about 50 mg.

In an embodiment of the method of treating MN, Form HB of LNP023 is administered to the subject at a daily total dose of about 200 mg, calculated as the anhydrous LNP023 free base. In an embodiment, the administration is twice daily (b.i.d.), e.g., about every 12 hours, of a dose of about 100 mg.

In an embodiment of the method of treating MN, Form HB of LNP023 is administered to the subject at a daily total dose of about 400 mg, calculated as the anhydrous LNP023 free base. In an embodiment, the administration is twice daily (b.i.d.), e.g., about every 12 hours, of a dose of about 200 mg.

In an embodiment of the method of treating MN, Form HB of LNP023 is administered orally to the subject twice daily (b.i.d.), e.g., about every 12 hours.

In an embodiment of the method of treating MN, Form HB of LNP023 is administered orally twice daily (b.i.d.), e.g., about every 12 hours, to the subject at a dose of 200 mg, calculated as the anhydrous LNP023 free base.

In another aspect, the invention relates to a method of treating atypically hemolytic uremic syndrome (aHUS) in a subject in need thereof, the method comprising administering a therapeutically effective amount of Form HB of LNP023 to the subject, to thereby treat the subject.

In an embodiment, the method of treating aHUS in the subject comprises administering Form HB of LNP023 to the subject at a daily dose of up to about 400 mg, calculated as the anhydrous LNP023 free base. In an embodiment, the administration is a twice daily (b.i.d.), e.g., about every 12 hours, dose of up to about 200 mg, calculated as the anhydrous LNP023 free base.

In an embodiment, the method of treating aHUS in the subject comprises administering Form HB of LNP023 to the subject at a daily dose of about 20 mg to about 400 mg, calculated as the anhydrous LNP023 free base. In an embodiment, the administration is twice daily (b.i.d.), e.g., about every 12 hours, of a dose of about 10 mg to about 200 mg, calculated as the anhydrous LNP023 free base.

In an embodiment, the method of treating aHUS in the subject comprises administering Form HB of LNP023 to the subject at a daily dose of about 20 mg, about 50 mg, about 100 mg, about 200 mg, or about 400 mg, calculated as the anhydrous LNP023 free base. In an embodiment, the administration is a twice daily (b.i.d.), e.g., about every 12 hours, dose of about 10 mg, about 25 mg, about 50 mg, about 100 mg, or about 200 mg, calculated as the anhydrous LNP023 free base.

In an embodiment of the method of treating aHUS, Form HB of LNP023 is administered to the subject at a daily total dose of about 20 mg, calculated as the anhydrous LNP023 free base. In an embodiment, the administration is twice daily (b.i.d.), e.g., about every 12 hours, of a dose of about 10 mg.

In an embodiment of the method of treating aHUS, Form HB of LNP023 is administered to the subject at a daily total dose of about 50 mg, calculated as the anhydrous LNP023 free base. In an embodiment, the administration is twice daily (b.i.d.), e.g., about every 12 hours, of a dose of about 25 mg.

In an embodiment of the method of treating aHUS, Form HB of LNP023 is administered to the subject at a daily total dose of about 100 mg, calculated as the anhydrous LNP023 free base. In an embodiment, the administration is twice daily (b.i.d.), e.g., about every 12 hours, of a dose of about 50 mg.

In an embodiment of the method of treating aHUS, Form HB of LNP023 is administered to the subject at a daily total dose of about 200 mg, calculated as the anhydrous LNP023 free base. In an embodiment, the administration is twice daily (b.i.d.), e.g., about every 12 hours, of a dose of about 100 mg.

In an embodiment of the method of treating aHUS, Form HB of LNP023 is administered to the subject at a daily total dose of about 400 mg, calculated as the anhydrous LNP023 free base. In an embodiment, the administration is twice daily (b.i.d.), e.g., about every 12 hours, of a dose of about 200 mg.

In an embodiment of the method of treating aHUS, Form HB of LNP023 is administered orally to the subject twice daily (b.i.d.), e.g., about every 12 hours.

In an embodiment of the method of treating aHUS, Form HB of LNP023 is administered orally twice daily (b.i.d.), e.g., about every 12 hours, to the subject at a dose of 200 mg, calculated as the anhydrous LNP023 free base.

All the aforementioned embodiments relating to the methods of treatment of certain diseases at particular doses are equally applicable to:

Form HB of LNP023 for use in the treatment of certain diseases at particular doses according to the present invention;

use of Form HB of LNP023 in the manufacture of a medicament for the treatment of certain diseases at particular doses according to the present invention;

the use of Form HB of LNP023 for the treatment of certain diseases at particular doses according to the present invention; and a pharmaceutical composition comprising Form HB of LNP023, and one or more pharmaceutically acceptable carriers, for use in the treatment of certain diseases at particular doses according to the present invention.

Test Methods for Morphological Properties

Aspect Ratio: The aspect ratio refers to the ratio of the maximum length of a crystal to its minimum width. At an aspect ratio of 1, a crystal has an isometric crystal habit. With the aspect ratio decreasing below 1, the crystal habit becomes more and more plate-like. In contrast, when the aspect ratio increases more and more above 1, the crystal approaches a needle-like crystal habit. In accordance with the disclosure, equant-shaped particles of Form HB have an aspect ratio $a_{50}$ of, e.g., between about 0.4 and about 0.7.

The aspect ratio is determined by means of a Dynamic Image Analysis (DIA) method using a QICPIC dynamic image analyzer from Sympatec GmbH, Clausthal-Zellerfeld, Germany. Particle size distribution: Particle size distribution is measured with laser light diffraction method (LLD) method using a Helos instrument from Sympatec GmbH, Clausthal-Zellerfeld, Germany.

Consolidated bulk density: The consolidated (15 kPa) bulk density is measured with an FT4 (Freeman Technology) powder rheometer.

EXAMPLES

The following non-limiting examples are illustrative for the disclosure and are not to be construed as to be in any way limiting.

Example 1: Preparation of Form HB of LNP023 Hydrochloride

Form A LNP023-HCl salt was obtained as described in Example 26d of WO 2015/009616. 9.3 g of Form A of LNP023 hydrochloride was suspended in 48.1 g of a mixture of acetone and water (acetone:water=78:22 m:m) and was dissolved at about 50° C. The solution was cooled to 40° C. and 136 g of a mixture of acetone and ethyl acetate (acetone:ethyl acetate=1:2 m:m) was added within 24 hours. The suspension was cooled to 10° C. to complete crystallization. The product was isolated by filtration, and dried under vacuum at 50° C. to give 7.7 g of the crystalline LNP023-HCl salt monohydrate (Form HB).

Example 2: Preparation of Form HB of LNP023 Hydrochloride Using Seed Crystals

Form A LNP023-HCl salt was obtained as described in example 26d of WO 2015/009616. 42 g of Form A of LNP023 hydrochloride was suspended in a 212 g mixture of acetone and water (acetone:water=80:20 m:m) and was dissolved at about 50° C. The solution was cooled to 25° C. and 0.4 g crystalline LNP023-HCl salt monohydrate (Form HB) seeds obtained in accordance with Example 1 were added to initiate crystal growth. Then 207 g acetone was added within 3 hours followed by 414 g ethyl acetate within 6 hours. The product was isolated by filtration, and dried under vacuum at 50° C. to give 36 g the crystalline LNP023-HCl salt monohydrate (Form HB).

Example 3: Preparation of Engineered Form HB of LNP023 Hydrochloride Using Temperature Cycles Form A LNP023-HCl salt was obtained as described in example 26d of WO2015/009616. 80 g of Form A of LNP023 hydrochloride was suspended in a 409 g mixture of acetone and water (acetone:water=78:22 m:m) and was dissolved at about 50° C. The solution was cooled to 40° C. and 0.32 g crystalline LNP023-HCl salt monohydrate (Form HB) seeds obtained in accordance with Example 1 were added to initiate crystal growth. Then temperature cycling was performed by cooling down to 10° C. and heating to 35° C. for 9 times. Then 1090 g ethyl acetate was added within 12 hours followed by cooling down to 5° C. The product was isolated by filtration, and dried under vacuum at 50° C. to give 66 g the crystalline LNP023-HCl salt monohydrate (Form HB) with columnar particles.

Example 4: Characterization of Form HB of LNP023 Hydrochloride

The title compound has the same $^1$H NMR spectrum as example 26d of WO2015/009616.
Exemplifications of Analyses and Interpretation of Results:
Powder X-Ray Diffraction PXRD was performed with a Bruker D8 Advance diffractometer with Bragg-Brentano geometry, Cu-Kalpha$_{1,2}$ radiation (wavelength 0.15419 nm) with a focusing mirror and a solid state PIXcel detector. The diffractogram was recorded at a tube voltage of 30 to 40 kV and a tube current of 40 mA, applying a stepsize of 0.015-0.020° 2-theta with an approximate step time of at least 40 s in the angular range of 2° to 40° 2-Theta at ambient conditions. A typical precision of the 2-theta values is in the range of ±0.2° 2-Theta, e.g., of ±0.1° 2-Theta. Thus, the diffraction peak of Form HB of LNP023 hydrochloride that appears for example at 9.2° 2-Theta can appear in the range of from (9.2-0.2°) to (9.2+0.2)° 2-Theta, e.g., from (9.2-0.1°) to (9.2+0.1)° 2-Theta on most X-ray diffractometers under standard conditions.

A representative diffractogram of Form HB of LNP023 hydrochloride is displayed in FIG. 1 herein. The corresponding peak list is provided in Table 2 below.

TABLE 1

PXRD peak positions and corresponding relative intensities of Form HB of LNP023 hydrochloride in the range of from 2 to 40° 2-Theta; a typical precision of the 2-Theta values is in the range of ±0.2° 2-Theta, e.g., of ±0.1° 2-Theta.

| Reflection position [° 2-Theta] | d-spacings (Å) | Relative intensity [%] |
|---|---|---|
| 4.6 | 19.22 | 14 |
| 6.8 | 13.01 | 12 |
| 9.2 | 9.58 | 19 |
| 10.0 | 8.81 | 48 |
| 12.2 | 7.25 | 18 |
| 12.6 | 7.01 | 19 |
| 15.3 | 5.80 | 16 |
| 16.6 | 5.33 | 100 |
| 17.2 | 5.15 | 26 |
| 19.1 | 4.64 | 26 |
| 20.7 | 4.29 | 42 |
| 21.3 | 4.17 | 22 |
| 22.2 | 3.99 | 29 |
| 24.0 | 3.70 | 54 |
| 24.6 | 3.62 | 25 |
| 28.0 | 3.18 | 33 |

The relative intensities as shown in Table 2 can be subject to a certain degree of variation due to the particle morphology of Form HB.
Fourier Transform Infrared Spectroscopy The FTIR spectrum was recorded with attenuated total reflectance (ATR) technique, with a Nicolet 6700 spectrometer with 4 cm$^{-1}$ resolution at RT. The number of scans was 64 and the range was 650 to 4000 wavenumbers (cm$^{-1}$).

To record a spectrum a spatula tip of the sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of from about ±2 cm$^{-1}$. Thus, the infrared peak of Form HB of LNP023 hydrochloride described herein at 3452 cm$^{-1}$ can appear between (3452-2) and (3452+2) cm$^{-1}$ on most infrared spectrometers under standard conditions.

A representative FTIR spectrum of the crystalline Form HB described herein is displayed in FIG. 3 and the corresponding peak list is provided below, with typical precision of the wavenumbers being in the range of ±2 cm$^{-1}$.
3452, 3274, 2933, 2875, 2732, 1709, 1692, 1658, 1615, 1601, 1515, 1497, 1461, 1439, 1425, 1384, 1243, 1184, 1069, 767, 739 cm$^{-1}$.
Differential Scanning Calorimetry DSC was performed on a TA Discovery DSC 2500 Instruments. The sample (2.7 mg) was heated in a Tzero aluminum pan with a pierced aluminum lid from 30 to 300° C. at a rate of 10° K/min. Nitrogen (purge rate 50 mL/min) was used as purge gas.

A representative DSC curve is displayed in FIG. 4 hereinafter and shows a broad endothermic event which ends at about 170° C., followed by exothermic decomposition at about 200° C., when measured at a heating rate of 10 K/min. More precisely, the endothermic event is in the range of 35° C. to 170° C.
Thermogravimetric Analysis TGA was performed on a Mettler Toledo DSC/TGA 1 instrument. The sample (10 to 20 mg) was heated in a100 microL aluminum pan closed with an aluminum lid from 30 to 300° C. at a rate of 20 K/min. The lid was automatically pierced at the beginning of the measurement. Nitrogen (purge rate 50 mL/min) was used as purge gas.

A representative TGA curve is displayed in FIG. 5 hereinafter and shows a step from about 30 to 220° C., which is due to the loss of water (dehydration) and residual solvents. The mass during the step was determined to be about 4.1%. The water content of 3.7% the sample was determined by Coulometric Karl-Fischer titration, which corresponds to 0.98 mole of water per mole LNP023 HCl. The water determination was performed on a Metrohm 831 KF Coulometer connected to a 774 Oven Sample Processor, which was heated to 160° C. for the measurement.

Dynamic Vapor Sorption

Dynamic vapor sorption isotherms were recorded with a DVS Advantage instrument. The measurement cycle was started at ambient relative humidity (RH) of 40%. RH was then decreased to 0% in 10% steps. Afterwards RH was increased from 0% to 90% in steps of 10% and from 90% to 95% in step of 5% in a sorption cycle and subsequently decreased to 0% in a desorption cycle each in 10% resp. 5% steps. Finally, RH was increased to ambient relative humidity of 40% in 10% steps. The time per step was set to a minimum of 3 hours and a maximum of 6 hours. If an equilibrium condition with a constant mass change of 0.002%/min for a minimum of 5 min was reached before the maximum time for all examined samples the sequential humidity step was applied before the maximum time of 6 hours. If no equilibrium was achieved the consecutive humidity step was applied after the maximum time of 6 hours. The temperature was 25±1.0° C.

FIG. 6 shows the equilibrium mass changes (delta m in weight %-reference weight at 0% RH on the y-axis) of Form HB of LNP023 hydrochloride during the sorption cycle (marked by triangles) from 0% to 95% RH, as well as during the desorption cycle (marked by squares) from 95 to 0% RH (on the x-axis). The mass difference between 40 and 95% RH is less than 0.2 weight % and no significant hysteresis between the sorption and desorption curve can be observed. Therefore, Form HB of LNP023 hydrochloride described herein can be assigned as being non-hygroscopic. The PXRD of Form HB of LNP023 hydrochloride remains unchanged after the experiment.

Electron Microscopy

Figure 7A:
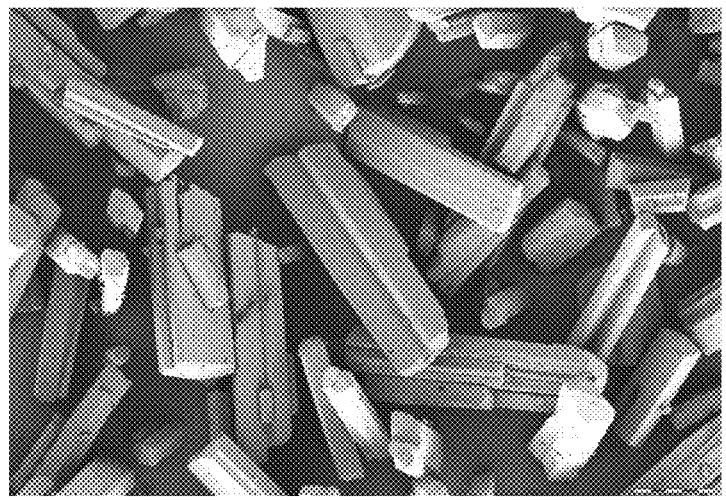
FIGS. 7a and 7b: illustrate scanning electron microscopic images of Form HB of LNP023 hydrochloride described herein when prepared according to Example 3 (scale bar overall: 50 micrometer).
Figure 7B:
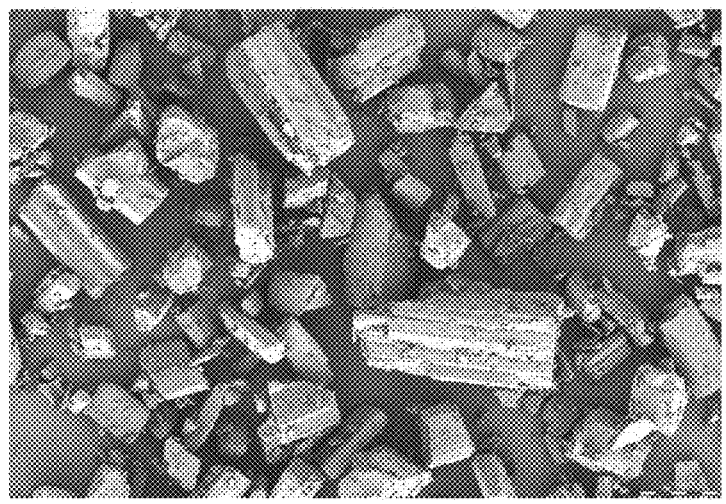

The electron microscopic images have been taken with a Gemini SE 300 (Zeiss) microscope using an SE detector. As can be seen in FIGS. 7a and 7b, Form HB of LNP023 hydrochloride obtained with engineered crystallization techniques, for example as shown in Example 3 comprises columnar and equant-like shaped particles, which explains the excellent flow properties of the powder.

Example 5: Preparation of Pharmaceutical Composition

Form HB particles as obtained in Example 3 are transferred to a 100 UPZ pin mill from Hosokawa Alpine AG, Augsburg/Germany. Particles are milled with a rotor speed of 6'000 rpm and a feed rate of 15 kg/h.

The obtained equant-like particles are filled in an amount of 50, 100 or 200 mg each into size 0 hard gelatin capsules.

The invention claimed is:

1. A crystalline hydrate form of a compound having Formula (A)

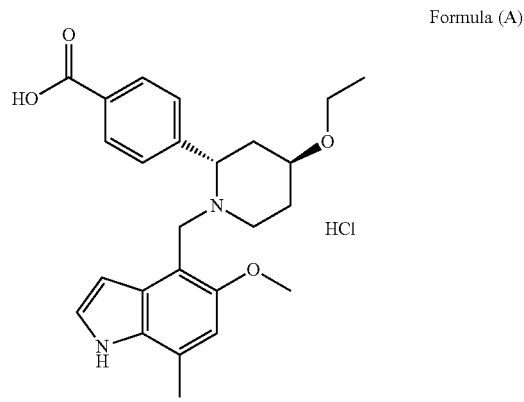 [SMILES: CCO[C@H]1CCN(Cc2c(OC)cc(C)c3[nH]ccc23)[C@H](c2ccc(C(=O)O)cc2)C1 ; Cl]

Formula (A)

characterized by having a powder X-ray diffractogram comprising peaks at 2-Theta angles of (4.6±0.2)°, (9.2±0.2)° and (19.1±0.2)°, when measured at a temperature in the range of from 20 to 30° C. with Cu-Kalpha$_{1,2}$ radiation having a wavelength of 0.15419 nm.

2. The crystalline hydrate form of claim 1, characterized by having a powder X-ray diffractogram comprising one or two peaks at 2-Theta angles of (6.8±0.2)° or (24.6±0.2)°, when measured at a temperature in the range of from 20 to 30° C. with Cu-Kalpha$_{1,2}$ radiation having a wavelength of 0.15419 nm.

3. The crystalline hydrate form of claim 1, characterized by having a Fourier transform infrared spectrum comprising peaks at wavenumbers of (3452±2) cm$^{-1}$, (2875±2) cm$^{-1}$, (1692±2) cm$^{-1}$, (1439±2) cm$^{-1}$ and (1243±2) cm$^{-1}$, when measured at a temperature in the range of from 20 to 30° C. with a diamond ATR cell.

4. The crystalline hydrate form of claim 1, characterized by having a differential scanning calorimetry curve comprising an endothermic event in the range of 35° C. to 170° C., when measured at a heating rate of 10 K/min.

5. The crystalline hydrate form of claim 1, characterized by having a thermogravimetric analysis curve showing a mass loss at a temperature of from 200 to 220° C., of not more than 4.5 w-%, based on the weight of the crystalline form, when heated from 30 to 300° C. at a rate of 20 K/min.

6. The crystalline hydrate form of claim 1, characterized by showing a mass change of not more than 4.5 w-%, based on the weight of the crystalline form at 0% RH, when measured with dynamic vapor sorption at a relative humidity in the range of from 0 to 95% and a temperature of (25±1.0)° C.

7. The crystalline hydrate form of claim 1, wherein the hydrate form is a monohydrate.

8. The crystalline hydrate form of claim 1, having a crystal habit which is essentially equant in shape.

9. A composition comprising the crystalline hydrate form of claim 1, wherein the composition comprises at most 20 weight %, 10 weight %, 5 weight %, 2 weight % or 1 weight % of any other physical form of the compound having Formula (A), based on the weight of the composition.

10. The composition according to claim 9, wherein the other physical form of the compound having Formula (A) is characterized by having a powder X-ray diffractogram comprising peaks at 2-Theta angles of (11.6±0.1)°, (15.3±0.1)°, (16.5±0.1)°, (20.1±0.1)° and (23.3±0.1)°, when measured at a temperature in the range of from 20 to 30° C. with Cu-Kalpha$_{1,2}$ radiation having a wavelength of 0.15419 nm.

11. A pharmaceutical composition comprising the crystalline hydrate form of claim 1, and optionally at least one pharmaceutically acceptable excipient.

12. The pharmaceutical composition of claim 11, which is an oral solid dosage form.

13. The pharmaceutical composition of claim 11, comprising the crystalline hydrate form having an aspect ratio between from about 0.4 to about 0.7.

14. The pharmaceutical composition of claim 11, comprising the crystalline hydrate form having a particle size distribution $X_{50}$ of from about 10 to about 70 µm.

15. The pharmaceutical composition of claim 11, comprising the crystalline hydrate form having a consolidated (15 kPa) bulk density from about 0.50 to about 0.65 g/ml.

16. The pharmaceutical composition of claim 11, wherein the composition comprises the compound having Formula (A) at a dose of up to about 200 mg, calculated as an anhydrous free base of the compound having Formula (A).

17. The pharmaceutical composition of claim 16, wherein the composition comprises the compound having Formula (A) at a dose of from about 10 mg to about 200 mg, calculated as the anhydrous free base of the compound having Formula (A).

18. The pharmaceutical composition of claim 16, wherein the composition comprises the compound having Formula (A) at a dose of about 10 mg, about 25 mg, about 50 mg, about 100 mg, or about 200 mg, each calculated as the anhydrous free base of the compound having Formula (A).

19. The pharmaceutical composition of claim 16, wherein the composition comprises the compound having Formula (A) at a dose of 10 mg, 25 mg, 50 mg, 100 mg, or 200 mg, each calculated as the anhydrous free base of the compound having Formula (A).

20. A process for preparing the crystalline hydrate form of claim 1, the process comprising:
  (i) providing the compound having Formula (A) in a solid form;
  (ii) suspending the compound having Formula (A) provided in step (i) in a first solvent comprising acetone and water and heating to dissolve the solid form to provide a solution;
  (iii) cooling the solution obtained in step (ii) and adding a second solvent comprising acetone, ethyl acetate, or a combination thereof, to provide crystals in a mother liquor;
  (iv) separating at least a part of the crystals obtained in step (iii) from the mother liquor to provide isolated crystals;
  (v) optionally washing the isolated crystals obtained in step (iv); and
  (vi) drying the crystals obtained in step (iv) or (v).

21. The process according to claim 20 comprising as step (iii)
  (a) cooling the solution obtained in step (ii) followed by re-heating the solution again;
  (b) repeating step (a) at least 3 times; and
  (c) adding a second solvent comprising acetone, ethyl acetate, or a combination thereof.

22. The crystalline hydrate form of claim 1, having a crystal habit which is columnar in shape.

23. The pharmaceutical composition of claim 11, which is a capsule.

* * * * *